US008672886B2

(12) United States Patent
Smit et al.

(10) Patent No.: US 8,672,886 B2
(45) Date of Patent: Mar. 18, 2014

(54) SYSTEM FOR USE DURING DISCOGRAPHY TO WIRELESSLY TRANSMIT DATA FROM HAND-HELD FLUID DELIVERY DEVICE INSIDE STERILE FIELD TO DEVICE OUTSIDE STERILE FIELD

(75) Inventors: Karen L. Smit, Kalamazoo, MI (US); Steven J. Carusillo, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 395 days.

(21) Appl. No.: 13/158,605

(22) Filed: Jun. 13, 2011

(65) Prior Publication Data

US 2011/0245760 A1 Oct. 6, 2011

Related U.S. Application Data

(62) Division of application No. 11/420,557, filed on May 26, 2006, now Pat. No. 7,959,607.

(60) Provisional application No. 60/685,466, filed on May 27, 2005.

(51) Int. Cl.
*A61M 37/00* (2006.01)

(52) U.S. Cl.
USPC ............................ 604/154; 604/920; 600/594

(58) Field of Classification Search
USPC .............. 604/100.01, 100.03, 151–154, 118, 604/187, 920; 600/587, 594, 430–432
See application file for complete search history.

(56) References Cited

U.S. PATENT DOCUMENTS

| 3,353,718 | A | 11/1967 | McLay |
| 4,583,974 | A | 4/1986 | Kokernak |
| 4,743,230 | A | 5/1988 | Nordquest |
| 4,781,192 | A | 11/1988 | Demer |
| 4,838,864 | A | 6/1989 | Peterson |
| 5,019,041 | A | 5/1991 | Robinson et al. |

(Continued)

FOREIGN PATENT DOCUMENTS

WO 2004075954 9/2004

OTHER PUBLICATIONS

International Search Report and Written Opinion dated Nov. 24, 2006; International filing dates May 26, 2006; International Application No. PCT/US2006/020519.

(Continued)

*Primary Examiner* — Laura Bouchelle
(74) *Attorney, Agent, or Firm* — Howard & Howard Attorneys PLLC

(57) ABSTRACT

A fluid delivery device is provided for delivering fluid to a target site such as an intervertebral disc during discography. The fluid delivery device includes pressure and volume sensors to determine the pressure and the volume of the fluid delivered to the intervertebral disc. The fluid delivery device is hand-held during use and includes a syringe assembly having a plunger with threads that enables controlled discharge of the fluid from the fluid delivery device by rotating the plunger in a housing of the fluid delivery device. The fluid delivery device includes a communication module to wirelessly transfer data to an external device outside of a sterile field, while the fluid delivery device is in the sterile field. The fluid delivery device may also include a physiological sensor to monitor involuntary pain responses based on changing physiological parameters such as increases in body temperature or blood pressure.

9 Claims, 21 Drawing Sheets

(56) References Cited

U.S. PATENT DOCUMENTS

| | | |
|---|---|---|
| 5,168,757 A | 12/1992 | Rabenau et al. |
| 5,259,838 A | 11/1993 | Taylor et al. |
| 5,279,563 A | 1/1994 | Brucker et al. |
| 5,300,031 A * | 4/1994 | Neer et al. ............... 604/154 |
| 5,318,534 A | 6/1994 | Williams et al. |
| 5,385,549 A | 1/1995 | Lampropoulos |
| 5,449,344 A | 9/1995 | Taylor et al. |
| 5,453,091 A | 9/1995 | Taylor |
| 5,472,424 A | 12/1995 | Lampropoulos et al. |
| 6,106,496 A | 8/2000 | Arnissolle |
| 6,370,420 B1 | 4/2002 | Kraft |
| 6,786,365 B2 | 9/2004 | Kim |
| 6,938,319 B2 | 9/2005 | Davis et al. |
| 7,291,131 B2 | 11/2007 | Call |
| 7,959,607 B2 * | 6/2011 | Smit et al. ............... 604/154 |
| 2002/0010431 A1 | 1/2002 | Dixon et al. |
| 2002/0120236 A1 | 8/2002 | Diaz et al. |
| 2002/0169439 A1 | 11/2002 | Flaherty |
| 2003/0055386 A1 | 3/2003 | Strauss et al. |
| 2004/0176984 A1 | 9/2004 | White et al. |
| 2004/0193045 A1 | 9/2004 | Scarborough et al. |
| 2004/0260238 A1 | 12/2004 | Call |
| 2005/0004518 A1 | 1/2005 | Call |

OTHER PUBLICATIONS

Frank J. Tomecek, MD, C. Scott Anthony, MD, Chris Boxell, MD, Jennifer Warren, CNS, "Discography Interpretation and Techniques in the Lumbar Spine", 2002, Neurosurg Focus 2002; 13(2), p. 5.

Smith & Nephew Endoscopy web page, CDS System, published before May 26, 2006, 4 pages.

* cited by examiner

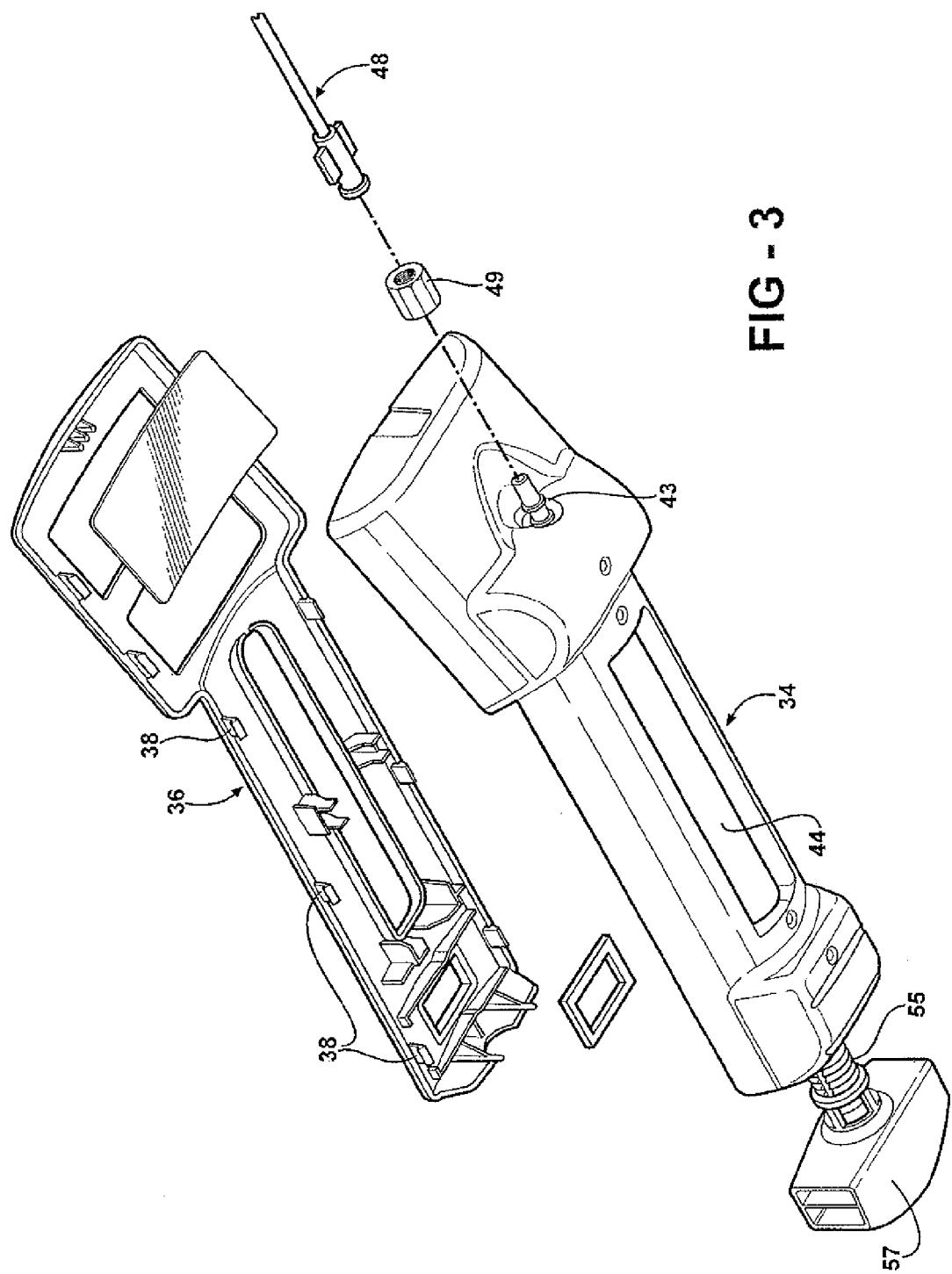

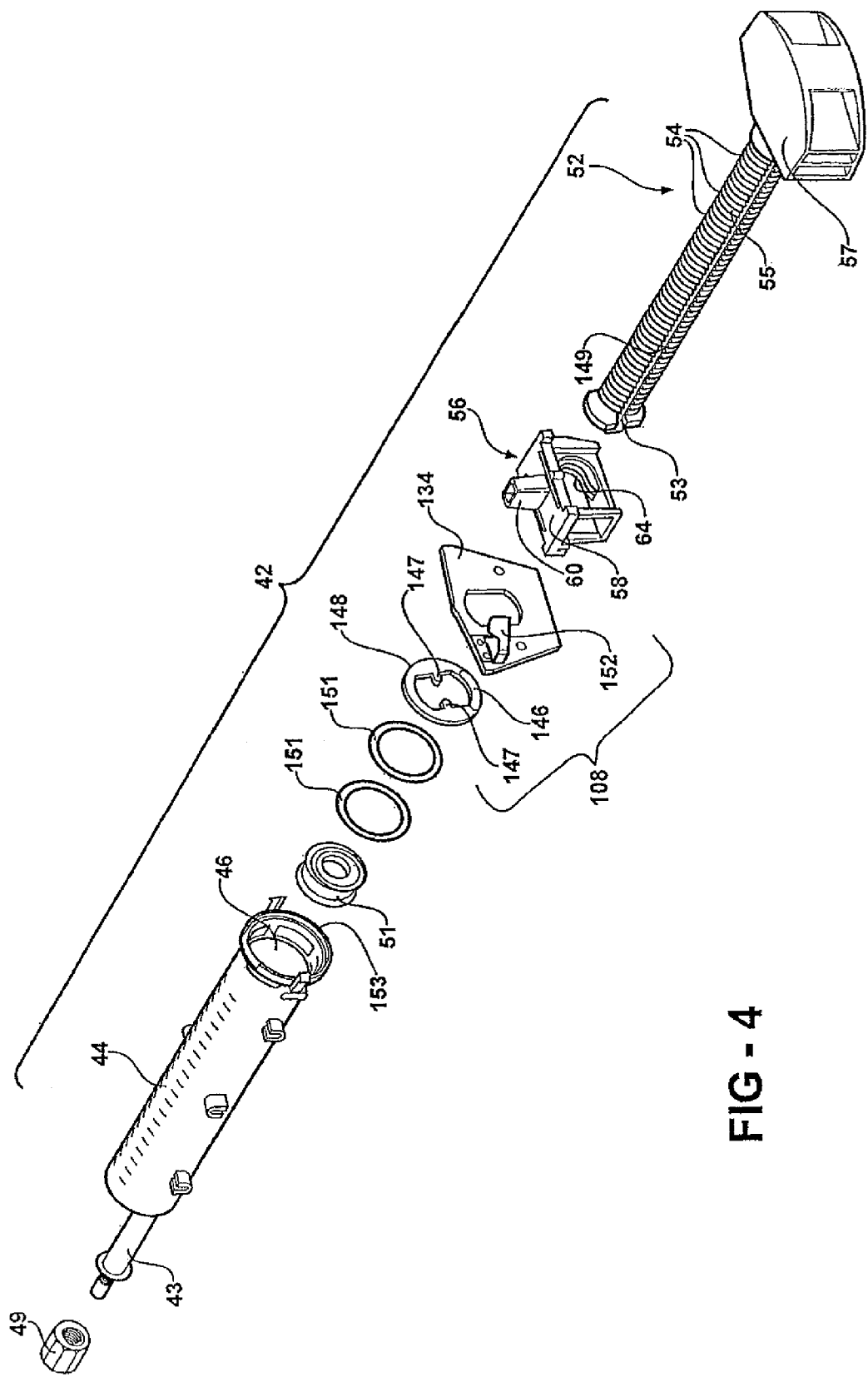

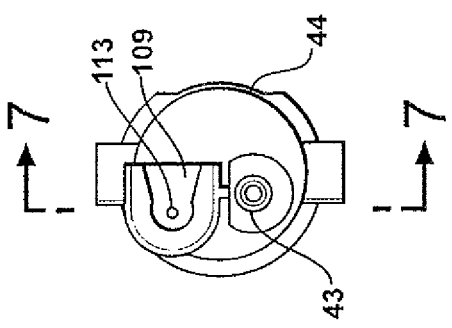
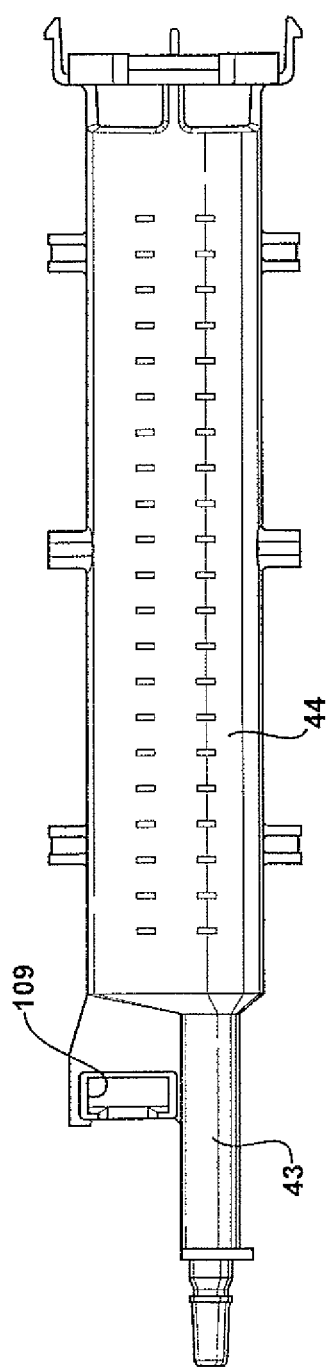
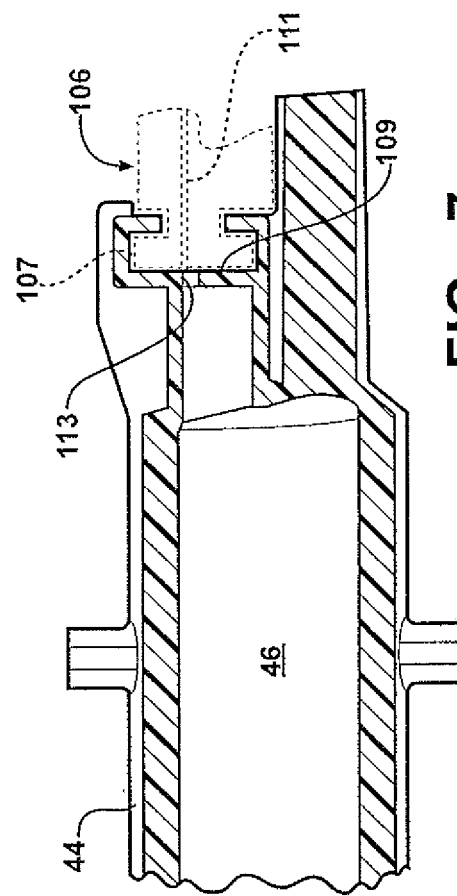

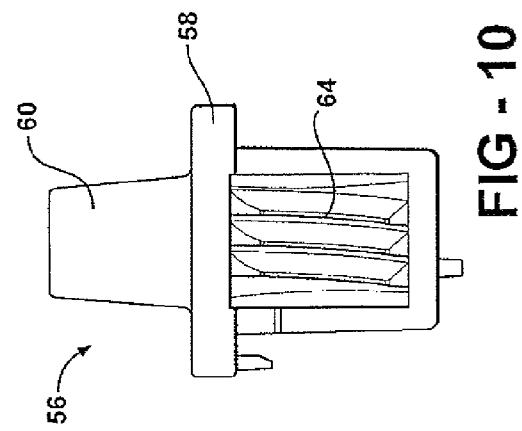
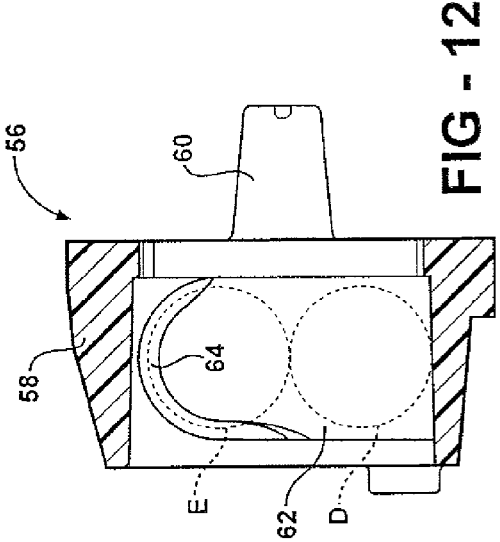
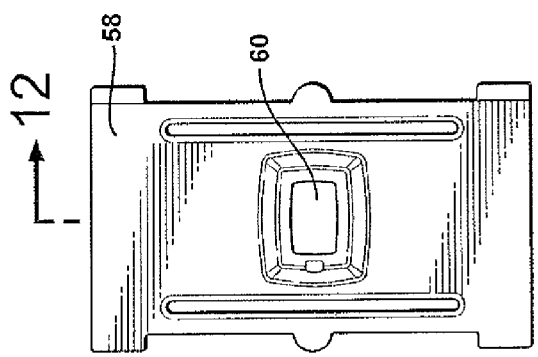
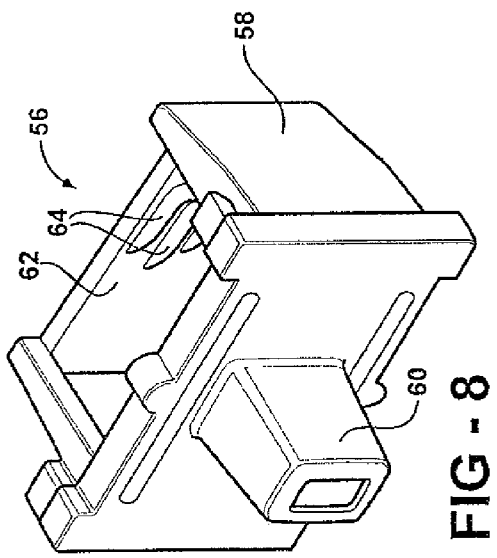
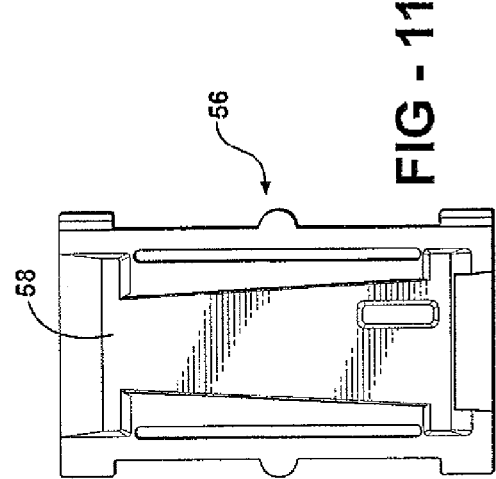

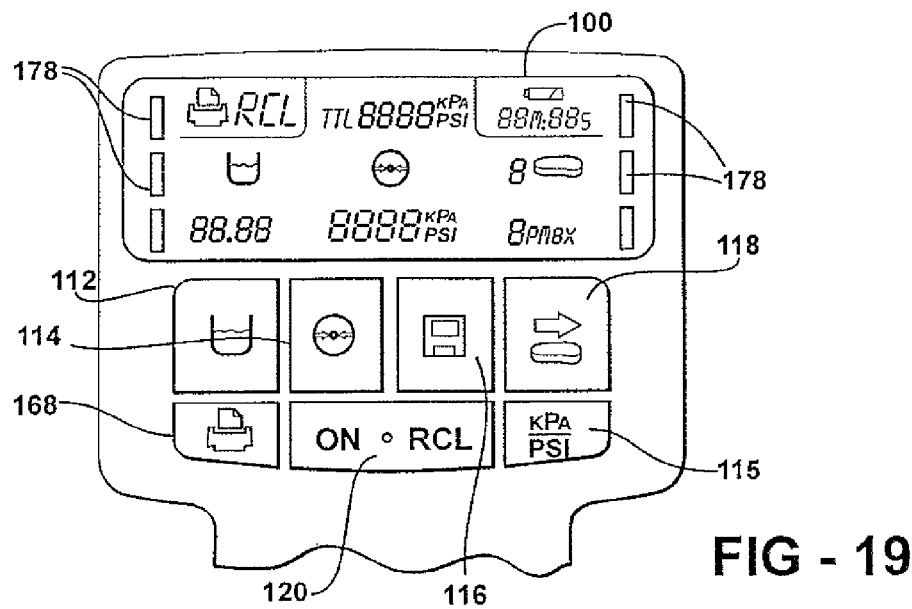
FIG - 19
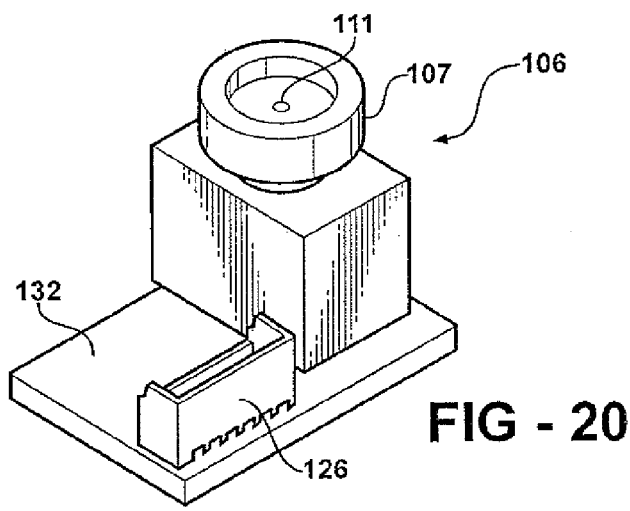
FIG - 20
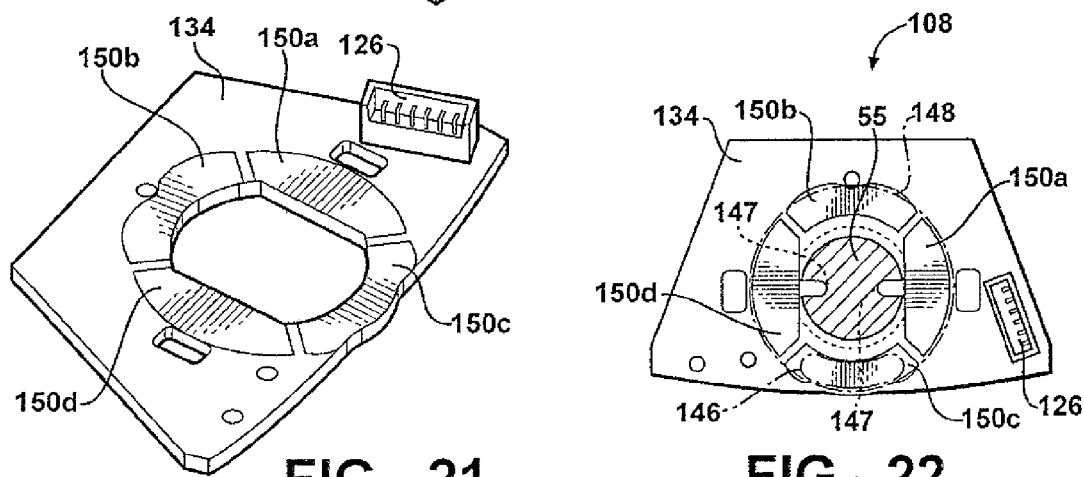
FIG - 21
FIG - 22

Time: _____    Date: _____

Patient ID: _____

1st Disc Level: _____

| Pts | Time (m:s) | TTL Press. PSI | Diff. Press. PSI | Volume mL |
|---|---|---|---|---|
| 1 | 01:25 | 25 | 15 | 01.60 |
| 2 | 02:00 | 45 | 35 | 02.05 |
| 3 | 02:35 | 70 | 70 | 02.40 |
| P0 | 00:10 | 10 | 00 | 00.30 |
| P0 | | | | |
| P0 | | | | |
| P0 | | | | |
| P0 | | | | |
| P max | 03:00 | 75 | 65 | 02.65 |
| V max | 03:05 | 73 | 63 | 02.70 |

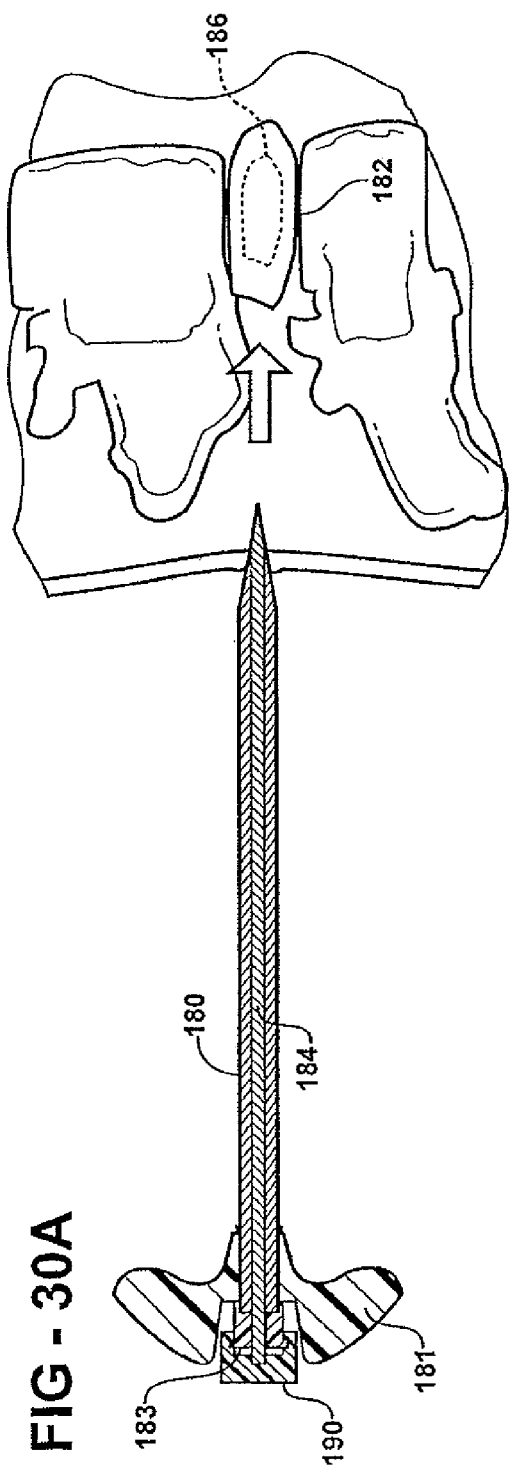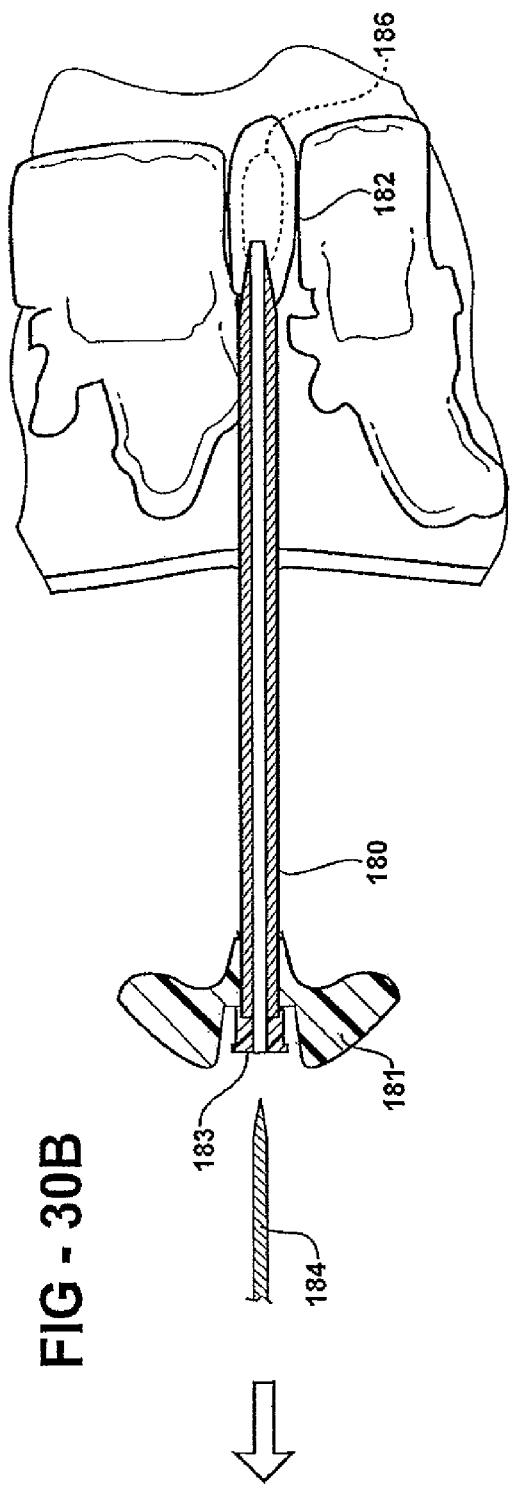

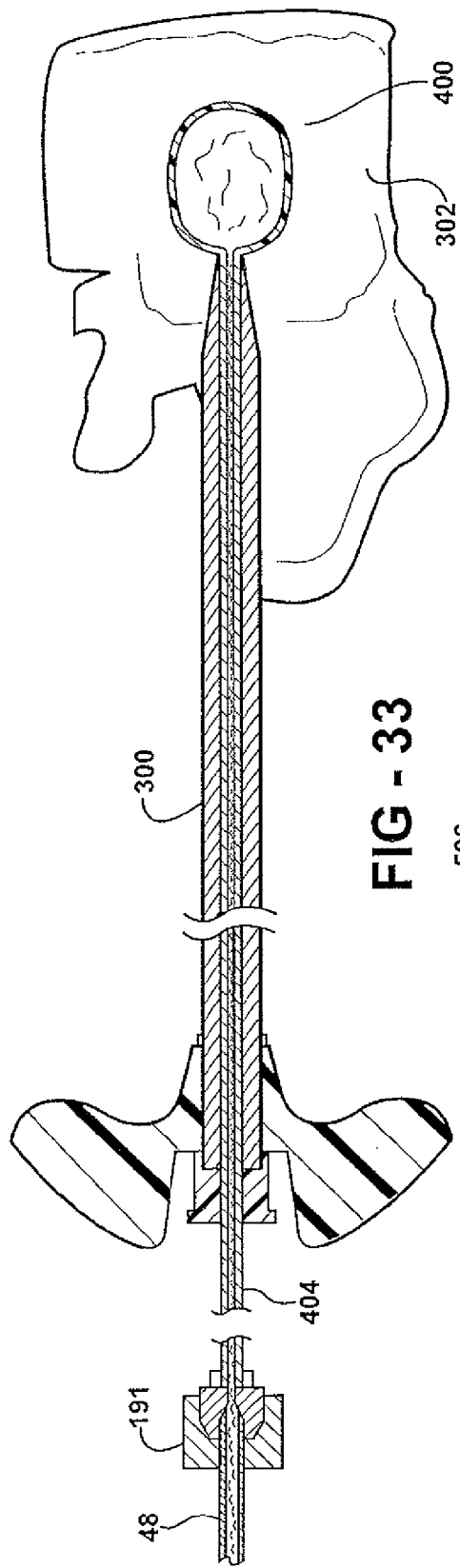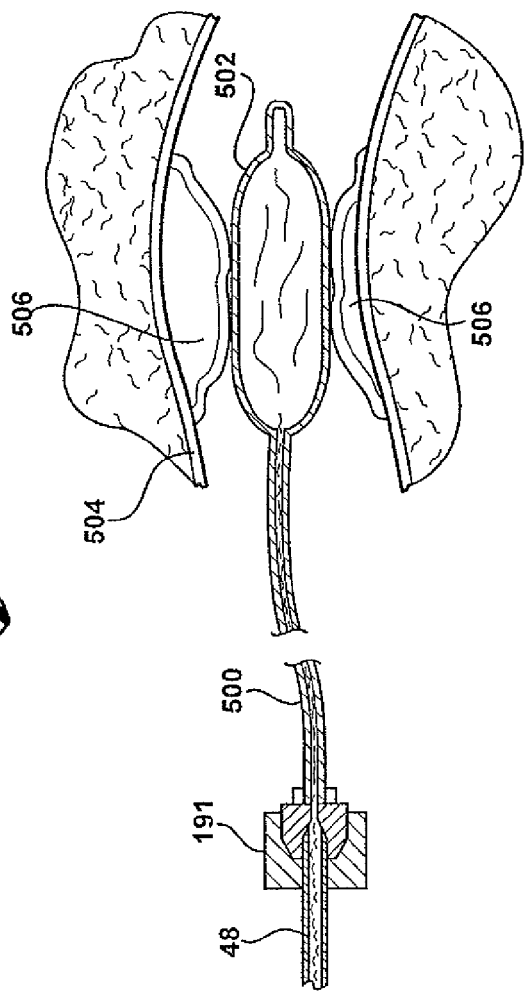
FIG - 33
FIG - 34

SYSTEM FOR USE DURING DISCOGRAPHY TO WIRELESSLY TRANSMIT DATA FROM HAND-HELD FLUID DELIVERY DEVICE INSIDE STERILE FIELD TO DEVICE OUTSIDE STERILE FIELD

CROSS-REFERENCE TO RELATED APPLICATIONS

This application is a divisional of U.S. patent application Ser. No. 11/420,557, filed May 26, 2006, which claims priority to U.S. Provisional Patent Application No. 60/685,466, filed May 27, 2005, the advantages and disclosure of both of which are hereby incorporated by reference.

FIELD OF THE INVENTION

The present invention generally relates to a fluid delivery device for delivering fluid to a target site. More specifically, the present invention relates to fluid delivery devices for use in medical procedures that benefit from monitoring and analyzing fluid pressures and volumes of fluid delivered to the target site. Examples of such medical procedures include, but are not limited to, discography, vertebroplasty, kyphoplasty, general injection of bone cement, angioplasty, and the like.

BACKGROUND OF THE INVENTION

There are a number of medical procedures in which fluid is permanently or temporarily delivered to a target site for medical treatment, diagnosis, and/or monitoring. In some of these procedures, medical professionals benefit from knowing the pressure at which the fluid is delivered to the target site. One such well-known procedure is an angioplasty procedure in which a balloon catheter is inserted into a blocked artery to be treated. Once the balloon catheter is in place, a balloon of the catheter is then inflated and deflated in one or more cycles to open the blocked artery and restore adequate blood flow through the artery. In this instance, pressure is monitored to ensure that the balloon is not under-inflated or over-inflated.

A fluid delivery device that has been found useful in monitoring pressure during an angioplasty is shown in U.S. Pat. No. 5,385,549 to Lampropoulus et al. The device of Lampropoulus et al. includes a housing defining a fluid chamber for storing the fluid and a plunger for sliding in the fluid chamber to discharge the fluid from the fluid chamber to the balloon catheter. The plunger is threaded such that an engagement mechanism can lock to threads on the plunger to restrict movement of the plunger to solely rotational movement. This provides controlled discharge of the fluid into the balloon catheter. The device also includes a pressure sensor for sensing a pressure of the fluid in the fluid chamber and a controller in communication with the pressure sensor to determine the value of the pressure in the fluid chamber. A display is in communication with the controller to display the value of the pressure. In one embodiment, the display may be located on the housing.

Another relatively new procedure that requires the delivery of fluid to a target site for isolating or diagnosing the cause of back pain is discography. Back pain can have a variety of causes. One known culprit is damaged or injured intervertebral discs. Intervertebral discs can be broadly described as fibrocartilage disposed between adjacent vertebrae of the spine. The fibrocartilage acts as a pad and supports the adjacent vertebrae. When an intervertebral disc is damaged or injured, back pain can result at least in part to pressure being applied to the intervertebral disc. Discography can be used to isolate damaged intervertebral discs.

During discography, a needle is inserted into an intervertebral disc suspected of causing the back pain and a contrast medium is injected into the disc through the needle. Using fluoroscopy, the physician can determine whether the contrast medium is properly positioned within the nucleus of the disc to get an idea about the health of the disc. If the disc is healthy, the contrast medium will stay in the nucleus. If the disc is damaged or degenerated, the contrast medium can spread easily throughout the disc. If the disc is ruptured, the contrast medium can actually discharge out of the nucleus. During the procedure, the patient is asked to respond if any pain is experienced, especially pain that mimics the condition that the patient is complaining of. The patient lets the physician know that there is pain and the level of pain by telling the physician the amount of pain experienced on a scale of 1 to 10.

Early discography procedures only measured a single factor, namely the level of pain response of the patient. However, improvements to this original procedure have been made. For instance, in U.S. Patent Application Publication No. 2004/0193045 to Scarborough et al., a fluid delivery device is described for use in discography that monitors both pressure and volume of fluid being delivered to the intervertebral disc. Other prior art devices used in angioplasty procedures, such as the device in Lampropoulus et al., only monitor pressure. Scarborough et al. teaches that information regarding both pressure and volume can be correlated with the pain experienced by the patient to better diagnose the condition of the disc being evaluated.

The fluid delivery device of Scarborough et al., however, is not designed to be lightweight, hand-held, and placed within the sterile field during use. In fact, the fluid delivery device of Scarborough et al. utilizes a motor-driven plunger (adding weight to the device) to drive the fluid from a fluid chamber to the intervertebral disc. Scarborough et al. also does not provide for the wireless transfer of data from the fluid delivery device in the sterile field to an external device outside of the sterile field and Scarborough et al. does not provide a fluid delivery device that reduces false pain indications, e.g., patients signaling pain when no actual pain is experienced.

Therefore, there remains a need in the art for a lightweight, hand-held device that is capable of delivering fluid to a suspect disc while monitoring fluid pressure and a volume of the fluid delivered. Finally, there is a need in the art for a fluid delivery device that is configured for transmitting data from the fluid delivery device in the sterile field to an external device outside of the sterile field.

SUMMARY OF THE INVENTION AND ADVANTAGES

A fluid delivery device for delivering fluid to an intervertebral disc during a discography procedure is provided. The fluid delivery device comprises a housing having a reservoir for storing the fluid. The housing has a hand-held portion for grasping by a user. A manually actuated pump is disposed in the housing and configured to pump the fluid from the reservoir. The pump includes a manual actuator for actuating the pump. A discography needle is configured for percutaneous insertion into the intervertebral disc to deliver the fluid from the reservoir to the intervertebral disc during the discography procedure. The discography needle has a length of at least 5 cm and an outer diameter of 16 gauge or smaller. A pressure sensor senses a pressure of the fluid in the reservoir and generates a pressure signal, while a volume sensor senses a volume of the fluid discharged from the reservoir and generates a volume signal. A controller is in communication with the pressure sensor and the volume sensor to receive the pressure and volume signals. The controller is also configured to output signals indicative of the pressure and the volume. A display is mounted to the housing and is in communication with the controller to receive the output signals and display indications of the pressure and the volume simultaneously on the display during the discography procedure. A battery is disposed in the housing for actuating the pressure sensor, the volume sensor, the controller and the display. The housing, including the reservoir, the pump including the actuator, the pressure sensor, the volume sensor, the controller, the display and the battery cumulatively have a weight of 1.5 kilograms or less.

In another aspect of the invention, an external module is provided for use with the fluid delivery device. The external module is spaced from the fluid delivery device, outside of the sterile field, and configured to receive data, e.g., pressure, volume, and time data, from the controller of the fluid delivery device (inside the sterile field). The external module is configured to transfer the data to a remote processing station that may be loaded with software to review, monitor, and/or manipulate the data.

In yet another aspect of the present invention, the fluid delivery device includes a physiological sensor for sensing a physiological parameter of the patient that is largely uncontrollable by the patient. The physiological parameter changes in response to the patient feeling pain to provide an involuntary pain indication. The controller is in communication with the physiological sensor to determine values of the physiological parameter and automatically mark a key value of the pressure, volume, and/or time, in response to the value of the physiological parameter exceeding a predetermined limit that is indicative of a predetermined pain level.

The present invention provides several advantages over the prior art. By providing a lightweight, hand-held device capable of monitoring both pressure and volume, a user can more easily maneuver the device in the sterile field while performing the discography procedure. This also enables the user to continuously monitor the pressure and volume values displayed on the display while performing the procedure. Other aspects of the present invention including the external module, the capability of performing the printing of data collected by the device by a printer that is wirelessly connected to the device and the physiological sensor, add to the improvement over the prior art.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 3 is a bottom partial exploded perspective view of the fluid delivery device of FIG. 1;

FIG. 4 is an exploded perspective view of a syringe assembly of the present invention;

FIG. 5 is a side view of a syringe barrel of the syringe assembly;

FIG. 6 is an end view of the syringe barrel;

FIG. 7 is a partial cross-sectional view taken generally along the line 7-7 in FIG. 6;

FIG. 8 is a perspective view of an engagement mechanism of the syringe assembly;

FIG. 9 is a top view of the engagement mechanism;

FIG. 10 is a side view of the engagement mechanism;

FIG. 11 is a bottom view of the engagement mechanism;

FIG. 12 is a cross-sectional view of the engagement mechanism taken generally along the line 12-12 in FIG. 9;

FIG. 19 is an illustration of a display of the fluid delivery device;

FIG. 20 is a perspective view of a pressure sensor with associated printed circuit board;

FIG. 21 is a perspective view of a volume sensor with associated printed circuit board;

FIG. 22 is a front view of the volume sensor illustrating with hidden lines a contact member of a rotating disc operatively coupled to the plunger;

FIGS. 30A-30D are illustrations of the fluid delivery device being used to perform a discography;

FIGS. 32-34 are examples of alternative uses of the fluid delivery device of the present invention.

DETAILED DESCRIPTION OF THE INVENTION

Referring to the Figures, wherein like numerals indicate like or corresponding parts throughout the several views, a fluid delivery device for delivering fluid to a target site during a medical procedure is generally shown at 30. The fluid delivery device 30 of the present invention is particularly useful in medical procedures in which it is beneficial to monitor and analyze fluid pressure and a volume of the fluid delivered to the target site. The fluid may be contrast media, bone cement, hydrogel, saline, or other fluid mediums that are delivered to target sites for medical monitoring, diagnosis, evaluation, and/or treatment.

Examples of medical procedures in which it may be beneficial to monitor and analyze pressure and volume include, but are not limited to, discography, vertebroplasty, kyphoplasty, general injection of bone cement, angioplasty, and the like. For purposes of illustration, the present invention will often be described for use in discography, i.e., diagnosing disc problems in intervertebral discs. More specifically, the fluid delivery device 30 will be described for use with pressurized contrast media to distend a patient's intervertebral disc. The fluid delivery device 30 displays critical information such as fluid pressure and volume of the fluid delivered, as well as desired information relating the patient's to back pain. This information can be stored or displayed in various ways and can be recalled, printed, or transferred to other devices as desired.

Figure 1:
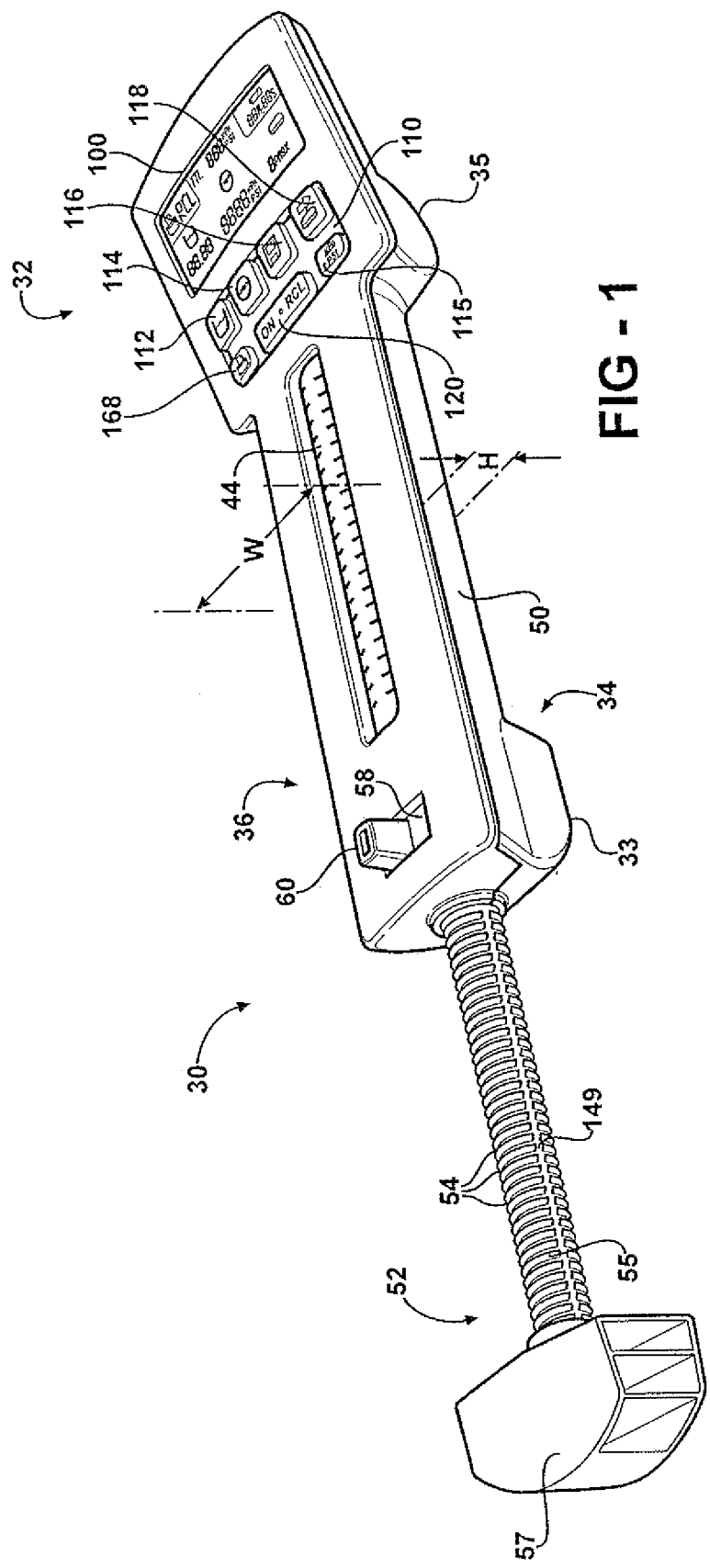
FIG. 1 is a top perspective view of a fluid delivery device of the present invention.
Figure 2:
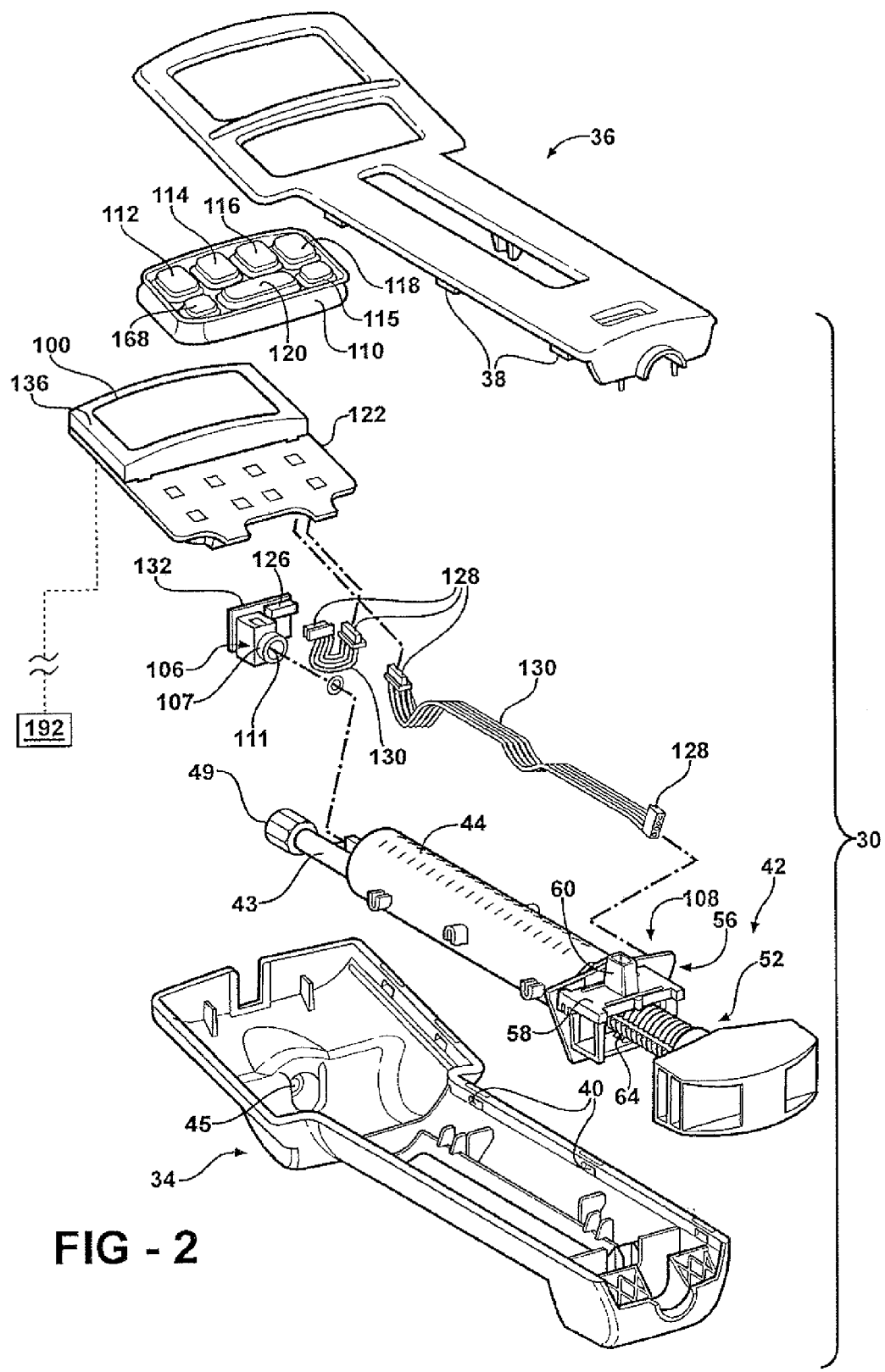
FIG. 2 is an top exploded perspective view of the fluid delivery device of FIG. 1.

Referring to FIGS. 1-3, the fluid delivery device 30 includes a housing 32 having a lower casing 34 and an upper casing 36 snap-fit to the lower casing 34 via a plurality of complimentary tabs 38 and notches 40. A syringe assembly 42 is captured between the upper 36 and lower 34 casings. The syringe assembly 42 includes a syringe barrel 44 that defines a fluid chamber 46 of the housing 32 to store the fluid to be delivered to the target site through a tube set 48. The housing 32 is preferably formed from a plastic material such as polycarbonate (PC), acrylonitrile butadiene styrene (ABS), high impact polystyrene (HIPS), and the like. The material used to form the housing 32 contributes to the lightweight nature of the fluid delivery device 30. Of course, other materials known to those skilled in the art could be used while maintaining the lightweight nature of the fluid delivery device 30. The fluid delivery device 30, as shown in FIG. 1, including the housing 32 and all components connected to (except the tube set 48), or internal to, the housing 32 described hereinafter, preferably has an unfilled weight (without fluid) of less than 1.5 kilograms, more preferably less than 0.5 kilograms, and most preferably less than 0.3 kilograms.

Referring specifically to FIG. 1, the housing 32 includes a proximal end 33 directed generally toward a user of the fluid delivery device 30 during use and a distal end 35 directed generally toward a patient during use. A hand-held portion 50 is disposed between the ends 33, 35. The hand-held portion 50 is configured for being held by the user during use. The hand-held portion 50 is further defined as a waist section of the housing 32 preferably having a smaller outer perimeter than at the proximal 33 and distal 35 ends. The hand-held portion 50 is dimensioned to be comfortably grasped in the palm of a hand of the user. This frees a second hand of the user to operate the fluid delivery device 30 as described further below. The hand-held portion 50 has a height H from about 0.3 to about 8.0 centimeters, more preferably from about 0.8 to about 5.0 centimeters, and most preferably from about 1.3 to about 3.0 centimeters. The hand-held portion 50 has a width W from about 0.3 to about 10 centimeters, more preferably from about 2.5 to about 8.0 centimeters, and most preferably from about 3.8 to about 6.5 centimeters. Thus, the hand-held portion 50 has an outer perimeter or girth that is comfortably sized to fit in the palm of the hand of the user during use. At least a portion of the syringe assembly 42 passes through the hand-held portion 50 to maximize space and minimize weight of the fluid delivery device 30.

Referring to FIGS. 2 and 4, the syringe assembly 42 is shown in more detail. In one embodiment, the syringe barrel 44 (preferably formed of plastic) has a volumetric capacity of 20 mL. It should be appreciated that other volumetric capacities could also be used depending on the particular procedure for which the fluid delivery device 30 is utilized. The syringe barrel 44 includes a nose section 43 at a distal end for positioning in an opening 45 in the lower casing 34. A threaded fitting 49 connects the tube set 48 to a tip of the nose section 43 to provide fluid communication between the fluid chamber 46 and the tube set 48.

The syringe assembly 42 also includes a plunger 52 having a distal end 53 disposed in the fluid chamber 46 for discharging the fluid from the fluid chamber 46 toward the target site as the plunger 52 moves in the fluid chamber 46 relative to the housing 32. The distal end 53 is fitted with an elastomeric seal member 51 to seal the distal end 53 in the fluid chamber 46 to prevent fluid from escaping out of the fluid chamber 46 past the distal end 53 of the plunger 52. The plunger 52 includes threads 54 disposed axially along a shaft 55 of the plunger 52. The threads 54 allow the user to carefully control movement of the plunger 52 within the housing 32 to discharge the fluid by rotating the plunger 52 relative to the housing. A handle 57 (or other manual actuator) is operatively coupled (preferably fixed) to a proximal end of the plunger 52 to facilitate grasping by the second hand of the user to move the plunger 52.

Engagement Mechanism

Referring to FIGS. 4 and 8-13, an engagement mechanism 56 controls operation of the plunger 52. The engagement mechanism 56 is supported by the housing 32 to engage the threads 54 of the plunger 52 in an engaged position E to allow only rotational advancement or retraction of the plunger 52 in the fluid chamber 46. The engagement mechanism 56 can also disengage from the threads 54 in a disengaged position D to allow slidable advancement or retraction of the plunger 52 in the fluid chamber 46. The engagement mechanism 56 includes a slide member 58 that is movable between the engaged E and disengaged D positions to lock to the threads 54 of the plunger 52 in the engaged position E and disengage from the threads 54 in the disengaged position D. The engaged and disengaged positions are best shown by the hidden lines E and D, respectively, in FIG. 12.

Referring to FIGS. 8-12, a toggle 60 is fixed to the slide member 58 and is configured for actuation by the user to move or slide the slide member 58 with a thumb and/or forefinger between the engaged and disengaged positions. The slide member 58 defines an opening 62 for receiving the threads 54 of the plunger 52. The slide member 58 includes control threads 64 extending into a first portion of the opening 62 to engage the threads 54 of the plunger 52 in the engaged position and the slide member 58 lacks control threads 64 in a second, opposite portion of the opening 62 to allow the threads 54 on the plunger 52 to freely slide through the opening 62 in the disengaged position. The slide member 58, including the integrally formed toggle 60, is preferably formed from a plastic material such as polycarbonate, acrylonitrile butadiene styrene (ABS), high impact polystyrene (HIPS), delrin, nylon and the like. The plastic material used to form the slide member 58 contributes to the lightweight nature of the fluid delivery device 30.

Figure 13:
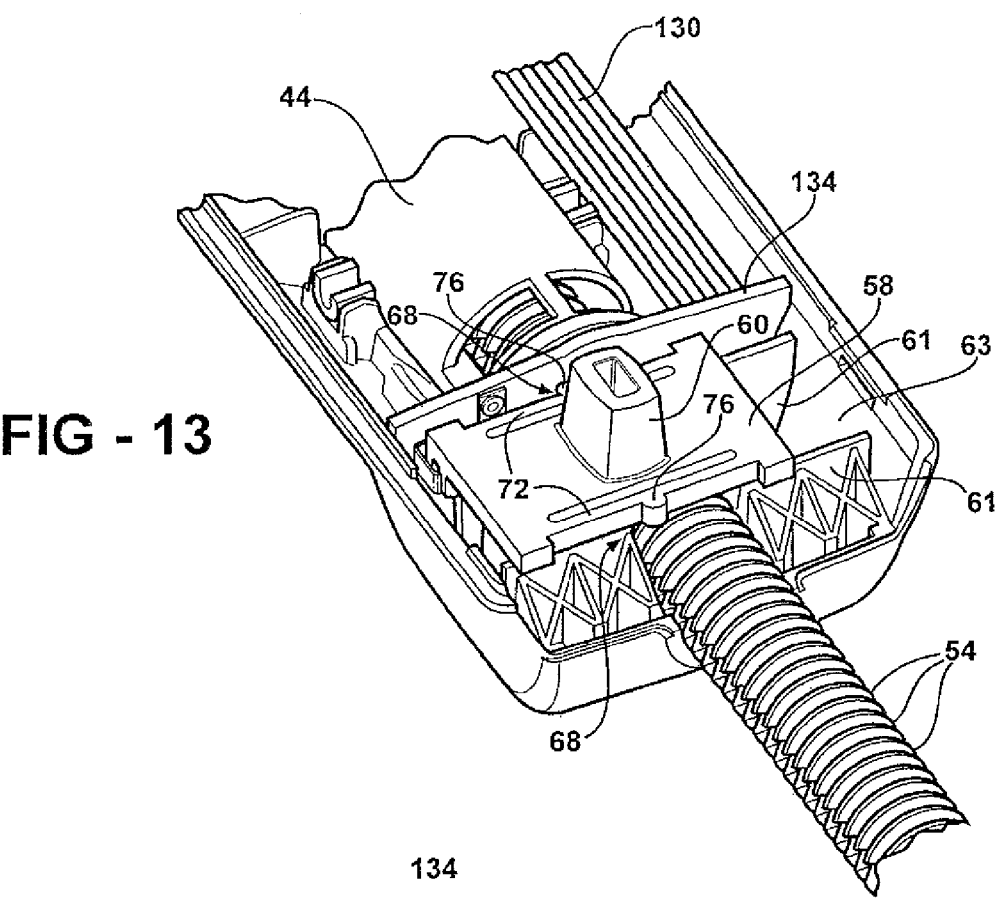
FIG. 13 is a top perspective view of the engagement mechanism seated in a lower casing of the housing in an engaged position.

Referring to FIG. 13, the slide member 58 is supported in a slide path 63 defined between two parallel side walls 61 disposed in the lower casing 34. The slide member 58 is slidable in the slide path 63 between the engaged E and disengaged D positions. The upper casing 36 (not included in FIG. 13) holds the slide member 58 from displacing out from the slide path 63 when actuated.

Figure 14:
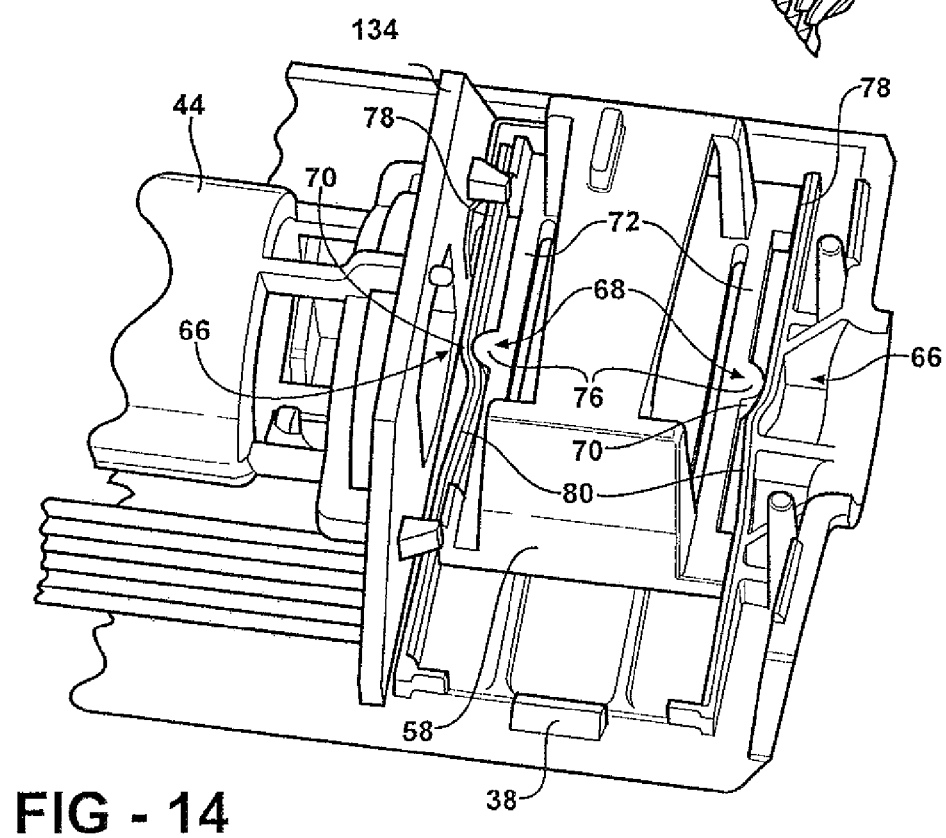
FIG. 14 is a bottom perspective view of the engagement mechanism in an upper casing of the housing in the engaged position.

Referring specifically to FIGS. 13 and 14, a restraining mechanism 66 is operable with the engagement mechanism 56 to restrain the slide member 58 in each of the engaged E and disengaged D positions as the slide member 58 is moved between the engaged E and disengaged D positions. Whether the slide member 58 engages the threads 54 on the plunger 52 is a discretionary choice by the user. However, with the restraining mechanism 66, once the slide member 58 is in place, the restraining mechanism 66 keeps the slide member 58 in either the engaged E or disengaged D position until the user determines that the slide member 58 should be moved.

Referring specifically to FIG. 14, the restraining mechanism 66 includes a first detent 68 mounted to the slide member 58 and a first detent pocket 70 for receiving the first detent 68 when the first detent 68 moves with the slide member 58 from the disengaged position D to the engaged position E. The first detent 68 is preferably integrally formed with the slide member 58 and includes an elongated, flexible member 72 spaced from a main body of the slide member 58 such that the flexible member 72 can flex relative to the main body. The first detent 68 also includes a projection 76 or bump approximately centered on the flexible member 72. The upper casing 36 of the housing 32 includes a first detent rail 78 defining the first detent pocket 70 and having a first ramp section 80. The projection 76 of the first detent 68 slides along the first detent rail 78 and over the first ramp section 80 to the first detent pocket 70 when the slide member 58 moves from the disengaged position D to the engaged position E.

The restraining mechanism 66 also includes a second detent 68, which is a minor image of the first detent 68, mounted to the slide member 58 and opposed from the first detent 68 and a second detent pocket 70 for receiving the second detent 68 when the second detent 68 moves with the slide member 58 from the disengaged position D to the engaged position E. The lower casing 34 of the housing 32 includes a second detent rail 78 defining the second detent pocket 70 and having a second ramp section 80, the second detent 68 being slidable along the second detent rail 78 and over the second ramp section 80 to the second detent pocket 70 when the slide member 58 moves from the disengaged position D to the engaged position E. The slide member 58 is shown in the engaged position E in FIG. 14.

Figure 15:
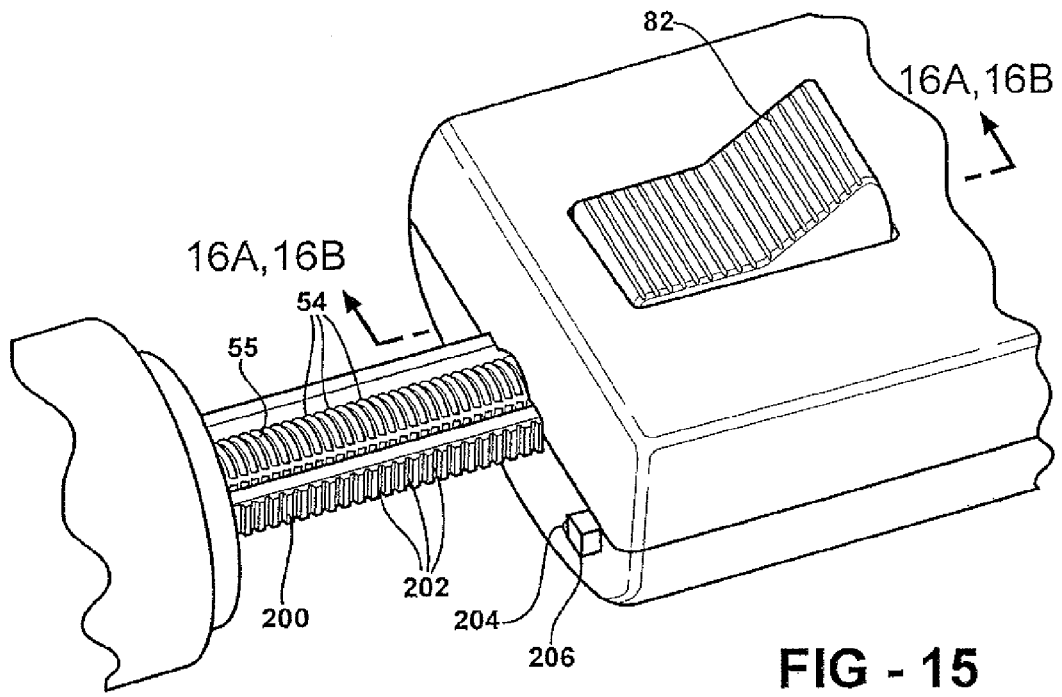
FIG. 15 is a perspective view of an alternative engagement mechanism of the present invention.
Figure 16A:
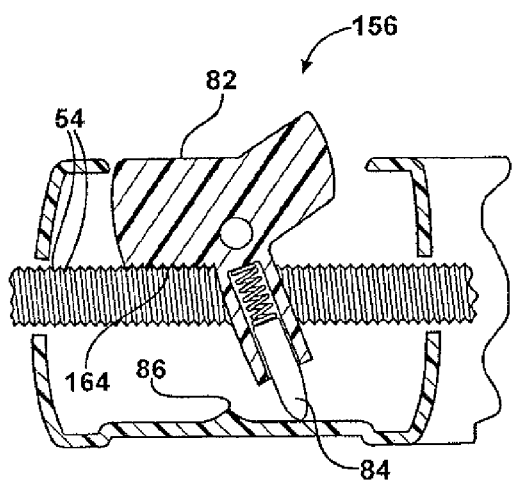
FIGS. 16A and 16B are partial cross-sectional views of the alternative engagement mechanism of FIG. 15 illustrating engaged and disengaged positions, respectively.
Figure 16B:
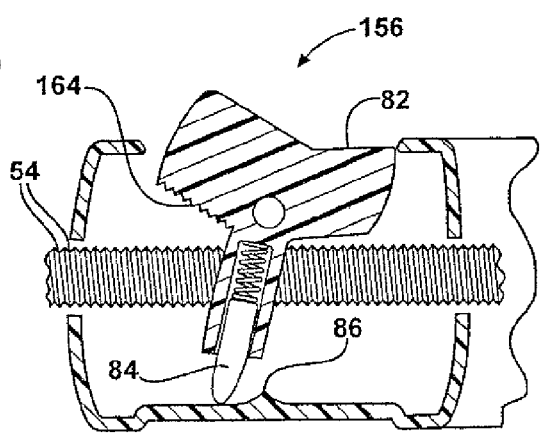

Referring to FIGS. 15, 16A, and 16B, an alternative engagement mechanism 156 and restraining mechanism is shown. In this embodiment, the slide member 58 is replaced by a control switch 82 having a spring-loaded pawl 84 that is adapted to snap over a boss 86 when the control switch 82 is pivoted about a pivot axis by the user between the engaged (FIG. 16A) and disengaged (FIG. 16B) positions. The spring-loaded pawl 84 acts as the restraining mechanism in this embodiment to maintain the control switch 82 in either position when moved. The control switch 82 has control threads 164 that are adapted to engage the threads 54 on the plunger 52 in the engaged position and disengage from the threads 54 in the disengaged position. The control switch 82 is pivotally supported about the pivot axis in the upper casing 36 of the housing 32.

Figure 17:
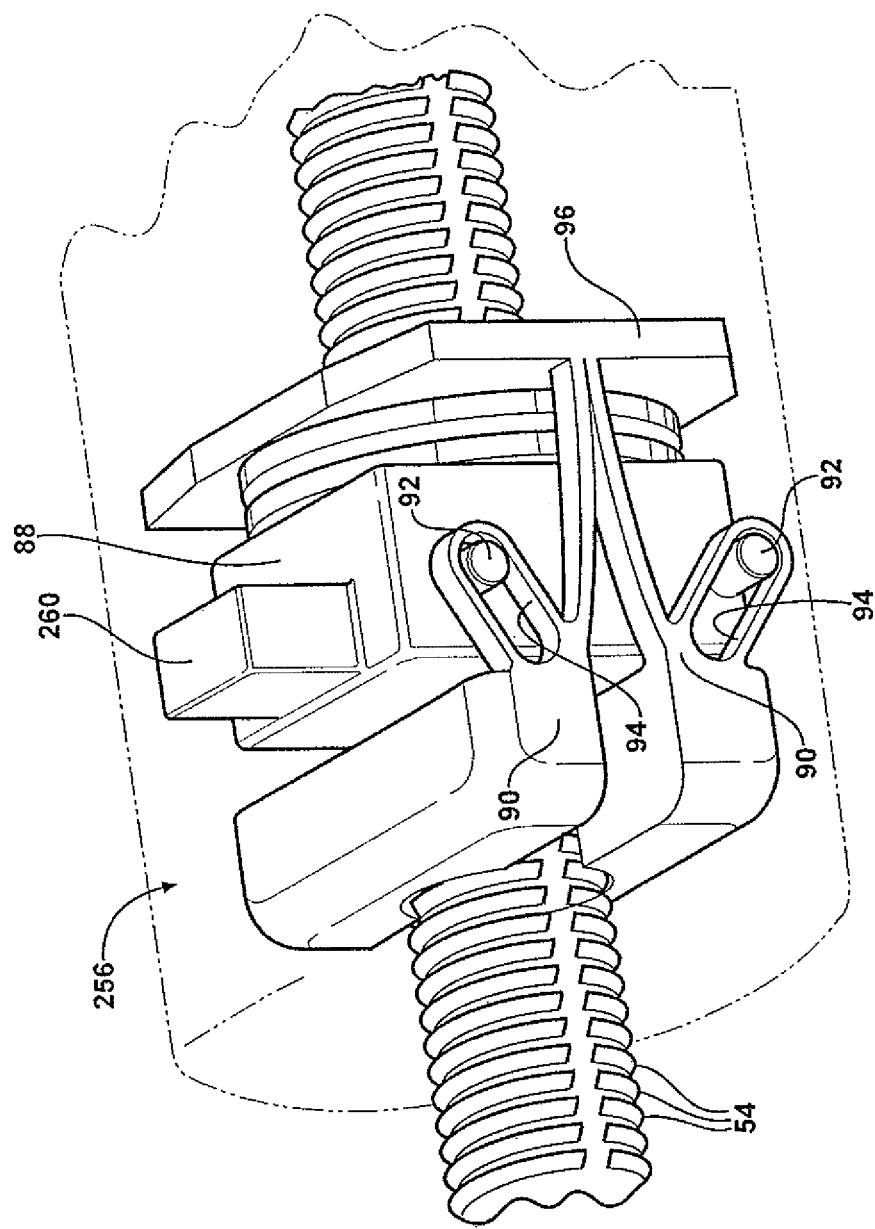
FIG. 17 is a perspective view of a second alternative engagement mechanism of the present invention.
Figure 18A:
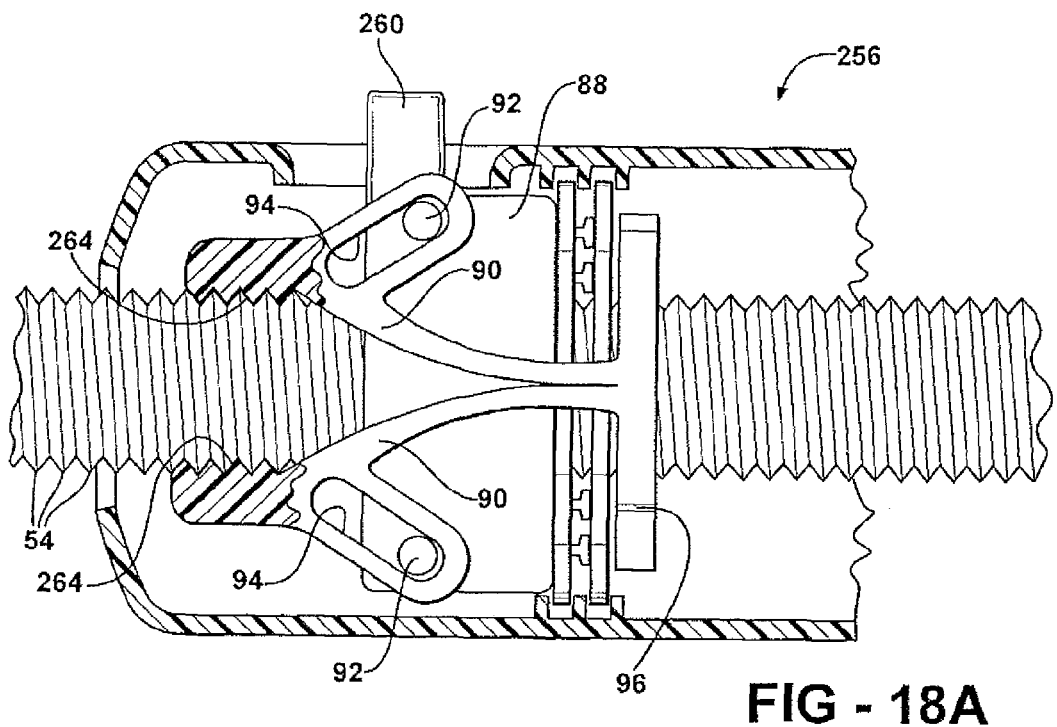
FIGS. 18A and 18B are partial cross-sectional views of the second alternative engagement mechanism of FIG. 17 illustrating engaged and disengaged positions, respectively.
Figure 18B:
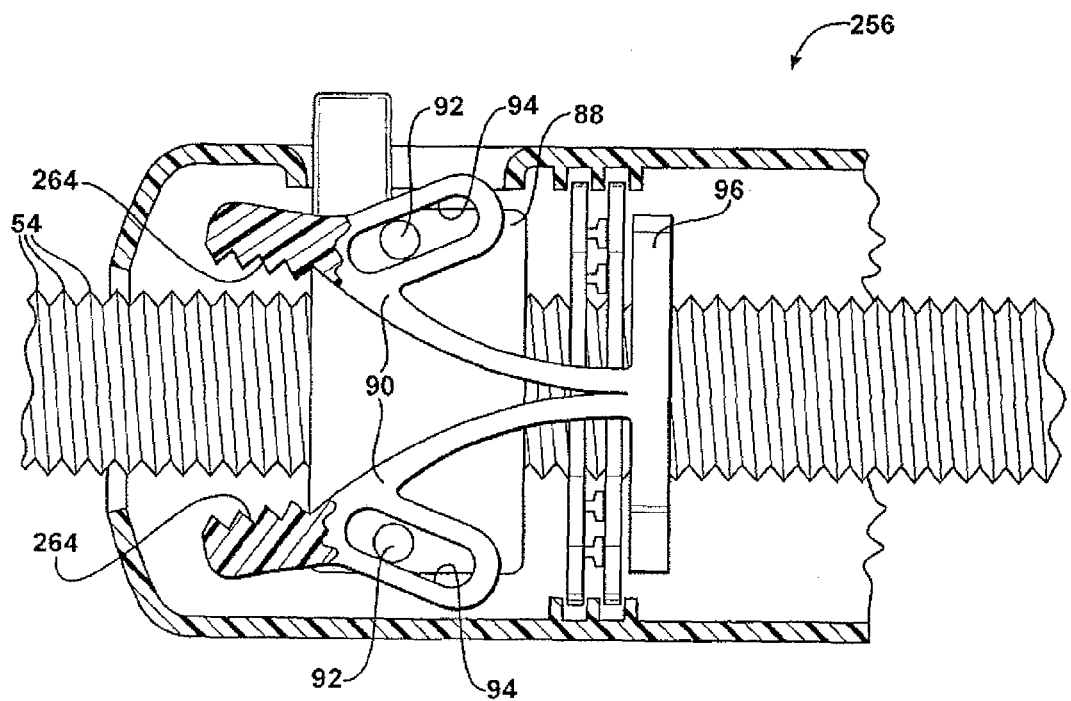

Referring to FIGS. 17, 18A, and 18B, a second alternative of the engagement mechanism 256 is shown. In this embodiment, the slide member 58 is replaced by an axially movable control member 88 that controls a pair of detent arms 90 having control threads 264. The control member 88 has pins 92 that engage slots 94 in the detent arms 90. The detent arms 90 have a connecting ring 96 or any other connecting method known to those of ordinary skill in the art to mount the detent arms 90 to the syringe assembly 42 about the threads 54 of the plunger 52. Each of the arms 90 has a head portion with control threads 264 that mate with the threads 54 on the plunger 52. The control member 88 can be moved axially forward and backward (proximally and distally) with respect to the housing 32 to force the detent arms 90 into engagement with the threads 54 or to allow the control threads 264 to move away from the threads 54 of the plunger 52. The detent arms 90 are biased in the engaged position in this embodiment. As will be appreciated by those of ordinary skill in the art, additional engagement mechanisms for switching between the engaged and disengaged positions could also be contemplated.

Control System

Referring to FIGS. 19-25, a control system of the fluid delivery device 30 is shown. The control system includes a display 100, a plurality of input devices 112, 114, 115, 116, 118, 120, 168, a controller 104 (e.g., microcontroller with microprocessor, memory, and other associated components), a pressure sensor 106 for sensing a pressure of the fluid in the fluid chamber 46, and a volume sensor 108 for sensing a volume of the fluid discharged from the fluid chamber 46.

The controller 104 is in communication with the pressure sensor 106 and the volume sensor 108 to determine values of the pressure and the volume of the fluid delivered to the target site, and the display 100 is in communication with the controller 104 such that the controller 104 can instruct the display 100 to display the determined values of pressure and volume simultaneously. The memory is used to save data during use including data relating to pressure, volume, and time. The controller 104 is configured for automatically saving key procedure data in the memory such as a maximum pressure reached during the procedure, a maximum volume discharged during the procedure, zeroed pressure, zeroed volume, and a maximum time. It should be understood that the memory internal to controller 104 is able to store data regarding the fluid injected into a plurality of individual discs during the course of a single procedure. Thus, each time the device is used to inject contrast media into a single disc 186, defined below as an "event," the controller memory stores data describing the volume of media injected, the pressure at which the media is injected and the points associated with the different levels of pain sensed by the patient.

Referring specifically to FIGS. 1 and 19, the display 100 is mounted between the upper and lower casings 36, 34 of the housing 32 at the distal end. More specifically, the display 100 is mounted at a proximally facing angle relative to a longitudinal dimension of the housing 32 to provide easy viewing by the user. The display 100 is configured to indicate a total pressure (e.g., total gauge pressure) of the fluid in the fluid chamber 46, a differential pressure of the fluid, a volume of the fluid discharged from the fluid chamber 46, a current event being monitored, e.g., disc 1 . . . disc 8, etc., a total time that pressure has been applied during that event (in some embodiments, the timer is not triggered until the total pressure exceeds a predetermined threshold such as 0.5 psi), and a total number of key data points recorded during that event. The display 100 also has a number of icons that indicate different operations of the fluid delivery device 30 such as a RCL icon that indicates previously recorded data has been recalled, and a printer icon that indicates data is being wirelessly transmitted to an external device such as a printer 160.

The plurality of input devices 112, 114, 115, 116, 118, 120, 168, also referred to as buttons or switches 112, 114, 115, 116, 118, 120, 168, are disposed beneath the display 100 on a keypad 110 (see FIG. 2). The keypad 110 protrudes into an opening in the upper casing 36 for actuation by the user during use. These selectable buttons or switches 112, 114, 115, 116, 118, 120, 168 are in communication with the controller 104 to carry out different operations of the fluid delivery device 30 when pressed by the user, as set forth below.

A volume tare switch 112 is configured to reset the value of the measured volume to zero upon actuation. The controller 104 is configured to display the reset or differential volume on the display 100. In some instances, it may be beneficial to display a volumetric flow rate on the display 100 in addition to the volume of the fluid discharged. This will allow the user to determine whether the fluid is being delivered to the target site, e.g., intervertebral disc, at a constant or variable rate. In some, but not all versions of the invention, the volume flow rate data are displayed as status bars 178 on the display.

A pressure tare switch 114 is configured to reset the value of the pressure to zero upon actuation to provide a differential pressure. When the pressure tare switch 114 is actuated, the controller 104 causes the display 100 to show both the total pressure, and a differential pressure. This "differential pressure" is the difference between total pressure and the pressure that was measured when switch 114 is actuated. As stated above, the display 100 always shows the total gauge pressure, which cannot be zeroed. During use, as the pressure continues to increase after the pressure tare switch 114 has been actuated, the display 100 then shows the increased pressure (differential pressure), while the display 100 continues to show the total gauge pressure. Thus, the controller 104 is configured to simultaneously display the differential pressure and the total pressure on the display 100 where the total pressure is based on a total value of the pressure unaffected by actuation of the selectable pressure tare switch 114. Both pressure values can be displayed in units of kPa or psi, changeable by pressing a unit switch 115. Alternative presentations of pressure can be in other units, BAR or ATM, for example.

A key data switch 116 is configured for marking key values of the data upon actuation. The controller 104 is configured to save the key values in the memory of the controller 104. In the disclosed embodiment of the present invention, the controller 104 automatically saves pressure (differential and total gauge), volume, and time data during the procedure. Additionally, key values of this data can be marked manually for each disc by pressing the key data switch 116. This allows the user to manually mark the pressure, volume, and time data at a specific point in the procedure. For example, the user may mark the data when the patient indicates that a certain pain threshold has been met, i.e., based on pain responses from the patient. The display 100 indicates the number of key data points that have been manually saved for the fluid injection process performed on each disc.

A new event switch 118, e.g., a next disc button, allows the user to segregate the data for different events, e.g., different discs that are evaluated. In other words, the controller 104 is configured to correlate separate data to each of a plurality of monitoring events, or discs in the case of discography. The total pressure, differential pressure, volume, and time may be reset to zero when the new event switch 118 is pressed so that new data for each new event is recorded. In any procedure, the physician can decide to move to a different event or disc for evaluation. In the event a different disc is selected, the physician can press the new event switch 118 to indicate that a different disc has been chosen. In one embodiment of the fluid delivery device 30, the user can name the specific disc by tabbing through various pre-installed disc names. The display 100 indicates that a different disc has been chosen.

An on/recall switch 120 is configured for turning the fluid delivery device 30 on to begin use or to recall the data saved during use. The controller 104 is configured such that once some data has been saved in the memory, upon actuation of the on/recall switch 120, the controller 104 selectively displays the data saved for each event, including the key values of the data saved for each key data point of each event saved during the procedure. Therefore, the on/recall switch 120 allows the user to access the saved data (manually saved data & automatically saved data) during the procedure and without requiring printing. The data is displayed on the display 100 while being recalled. The recalled data scrolls automatically or manually depending on how the user presses the on/recall switch 120. When the user presses and holds the on/recall switch 120, scrolling is automatic. Otherwise, each press of the on/recall switch 120 manually advances to the next key data point or to the next saved event. The on/recall switch 120 can, for example, scroll through maximum pressure, maximum volume, zeroed pressure, key data values for multiple key data points, for each disc. The display 100 indicates what data is currently being shown when in the recall mode. It is understood that the "on" and "recall" functionality of the on/recall switch 120 could be separated into two different switches.

Figure 23:
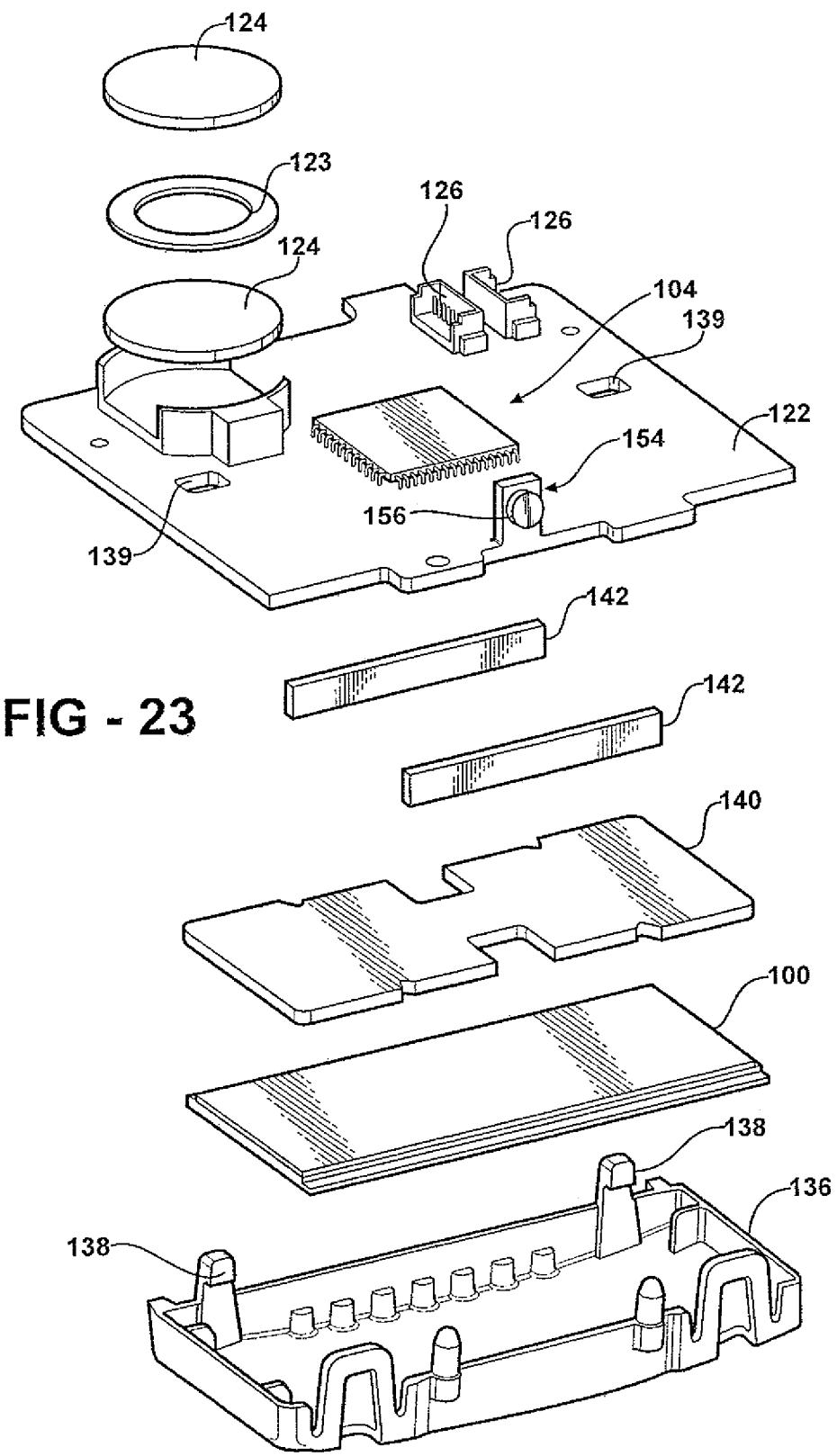
FIG. 23 is an exploded view of a main electronic assembly of the fluid delivery device.

Referring to FIG. 23, a main printed circuit board (PCB) 122 of the control system is shown. The main PCB 122 carries one or more batteries 124. The fluid delivery device 30 is preferably cordless such that the batteries 124 provide all of the power needed by the fluid delivery device 30 and the communications connection to the final data storage device is wireless. The fluid delivery device 30 is also configured to conserve battery power by providing a power down mode after a predetermined time period, described further below. The main PCB 122 also includes connectors 126 for receiving connecting ends 128 of cables 130 used to electronically couple electronic components on the main PCB 122. The pressure sensor 106 and associated components are disposed on a second PCB 132, which is electrically coupled to the main PCB 122. The volume sensor 108 and associated components are disposed on a third PCB 134, which is electrically coupled to the main PCB 122. The second PCB 132 and the third PCB 134 also include connectors 126 for receiving a connecting end 128 of cables 130 interconnecting the second PCB 132 and the third PCB 134 to the main PCB 122.

The display 100 is shown mounted in a cage 136. The cage 136 snap-fits to the main PCB 122 via corresponding snap-fit connectors 138 and notches 139. A spacer 140 and elastomeric mounts 142 can be used to secure the display 100, preferably a LCD display 100, in the cage 136.

Referring to FIG. 20, the pressure sensor 106 is shown in more detail. The pressure sensor 106 is mounted to the second PCB 132. The connector 126 on the second PCB 132 is used to place the pressure sensor 106 in communication with the controller 104 of the control system such that the controller 104 can determine values of pressure based on control signals from the pressure sensor 106. In the preferred embodiment, the pressure sensor 106 is a Honeywell 26PCFFS2G electronic pressure sensor 106 with a pressure sensing frequency of once every 147 mS.

Referring briefly to FIG. 7, the pressure sensor 106 is shown fitted to the syringe barrel 44. The pressure sensor 106 has a hub 107 fit into a receiving pocket 109 on the syringe barrel 44. The hub 107 is sealed in the receiving pocket 109 to prevent fluid from leaking out of the fluid chamber 46 around the pressure sensor 106. The hub 107 may also be fixed in the receiving pocket 109 with an adhesive, snap-fit connection, or the like. The pressure sensor 106 senses the pressure in the fluid chamber 46 through a sensing orifice 111 that is in communication with the fluid chamber 46 via a passage 113. Other methods of placing the pressure sensor 106 in contact with the fluid in the fluid chamber 46 could also be contemplated. As will be appreciated by those of ordinary skill in the art, other electronic sensors or methods of sensing pressure could be used. Also, it should be appreciated that since the pressure sensor 106 is in direct fluid communication with the fluid chamber 46, the measured pressure is the pressure of the fluid in the fluid chamber 46.

Referring to FIGS. 21 and 22, the preferred embodiment of the volume sensor 108 is shown. In this embodiment, the volume of the fluid discharged from the fluid chamber 46 is measured by detecting rotation of the plunger 52 relative to the housing 32. In this embodiment, the volume sensor 108 includes a contact member 146 (shown by hidden lines in FIG. 22) coupled to the shaft 55 of the plunger 52 to rotate with the plunger 52 during the rotational advancement of the plunger 52. The contact member 146 is mounted to a rotating disc 148 (shown by hidden lines in FIG. 22) fixed about the plunger 52 by two tabs 147 that ride in grooves 149 defined in the shaft 55 of the plunger 52. Spring washers or bushings 151 having slightly wavy and flexible undulations are used to rotatably mount the rotating disc 148 in an annular shoulder pocket 153 defined in an open proximal end of the syringe barrel 44. The spring washers 151 hold the rotating disc 148 tightly against the third PCB 134, as the rotating disc 148 rotates relative to the third PCB 134.

The volume sensor 108 further includes a plurality of sensing members 150a, 150b, 150c, 150d fixed to the third PCB 134. The controller 104 measures the volume by sensing a rotational position of the contact member 146 relative to the sensing members 150a, 150b, 150c, 150d as the contact member 146 rotates with the plunger 52. In essence, the contact member 146 completes a circuit between any two of the sensing members 150a, 150b, 150c, 150d when simultaneously contacting any two of the sensing members 150a, 150b, 150c, 150d. The controller 104 is configured, as described further below in reference to FIGS. 24A, 24B, and 25, to determine the rotational position of the contact member 146 when the contact member 146 is in contact with any two of the sensing members 150a, 150b, 150c, 150d. The controller 104 is also capable of determining whether the plunger 52 is rotating clockwise to discharge the fluid (adding an incremental volume amount to the total volume measured) or if the plunger 52 is rotating counterclockwise, which backs-off fluid delivery (subtracting an incremental volume amount from the total volume measured).

Accuracy of volume measurement can be increased by increasing the number of sensing members 150a, 150b, 150c, 150d mounted to the third PCB 134. In the embodiment shown, four sensing members 150a, 150b, 150c, 150d are used to determine the volume. Thus, in the instance in which the plunger 52 discharges 0.5 cc or mL with every full rotation of the plunger 52, the best resolution of the volume sensor 108 is 0.125 cc or mL. In other words, the controller 104 is capable of identifying the contact member 146 at four positions for each full revolution.

As pressure increases, the volume measurement may be obscured by changes in shape of the seal member 51 of the plunger 52, or other compressible components. Likewise, the presence of air bubbles in the fluid may affect volume measurement. Thus, the controller 104 may be programmed to nominally account for such changes in volume based on a predetermined adjustment factor.

In an alternative embodiment (not shown), the volume is determined by a circuit board with three switches mounted to the circuit board under the shaft 55 of the plunger 52. Two of the switches click against notches cut in the threads 54 every 36 degrees. The third switch senses if the slide member 58 is in the disengaged position in order to set the volume reading to zero when the threads 54 are disengaged. Two more switches could be added to the circuit board to sense translation and achieve a reading in the disengaged position.

In yet another alternative embodiment (see FIG. 15), the volume is determined with the use of a plastic cage 200 that travels with the shaft 55 of the plunger 52, but does not rotate. Sides of the plastic cage 200 are encoded with indentations 202 every 0.01 inches. An LED 204 shines on the indentations 202. An optical sensor 206 reads the reflections off the plastic surface and sends a corresponding signal back to the controller 104. The controller 104 then counts the number of indentations 202 sensed to determine volume (each indentation 202 corresponds to a predetermined amount of fluid delivered).

Figure 24A:
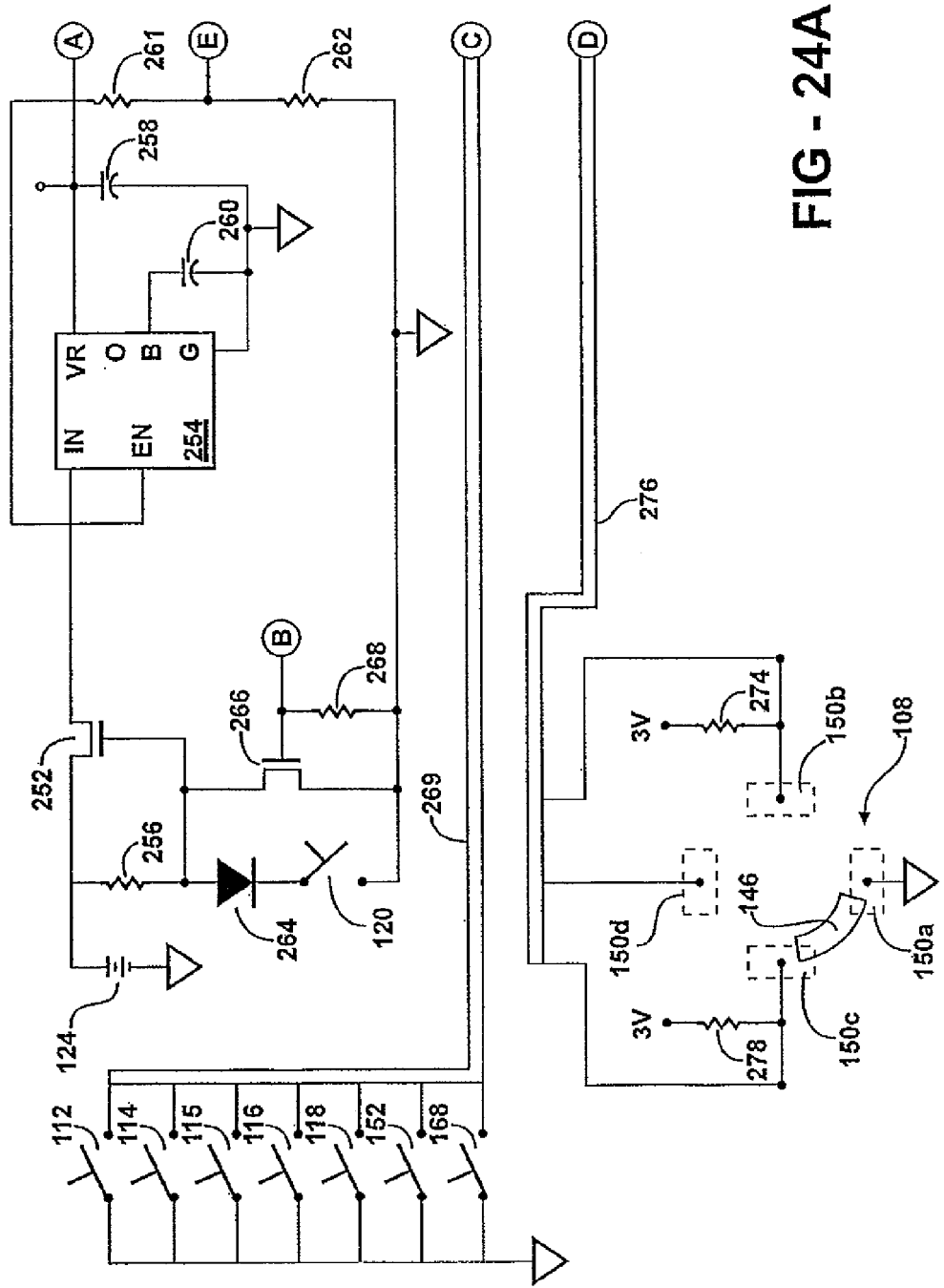
FIGS. 24A and 24B are electrical schematics of electronic components of the fluid delivery device of FIG. 1.
Figure 24B:
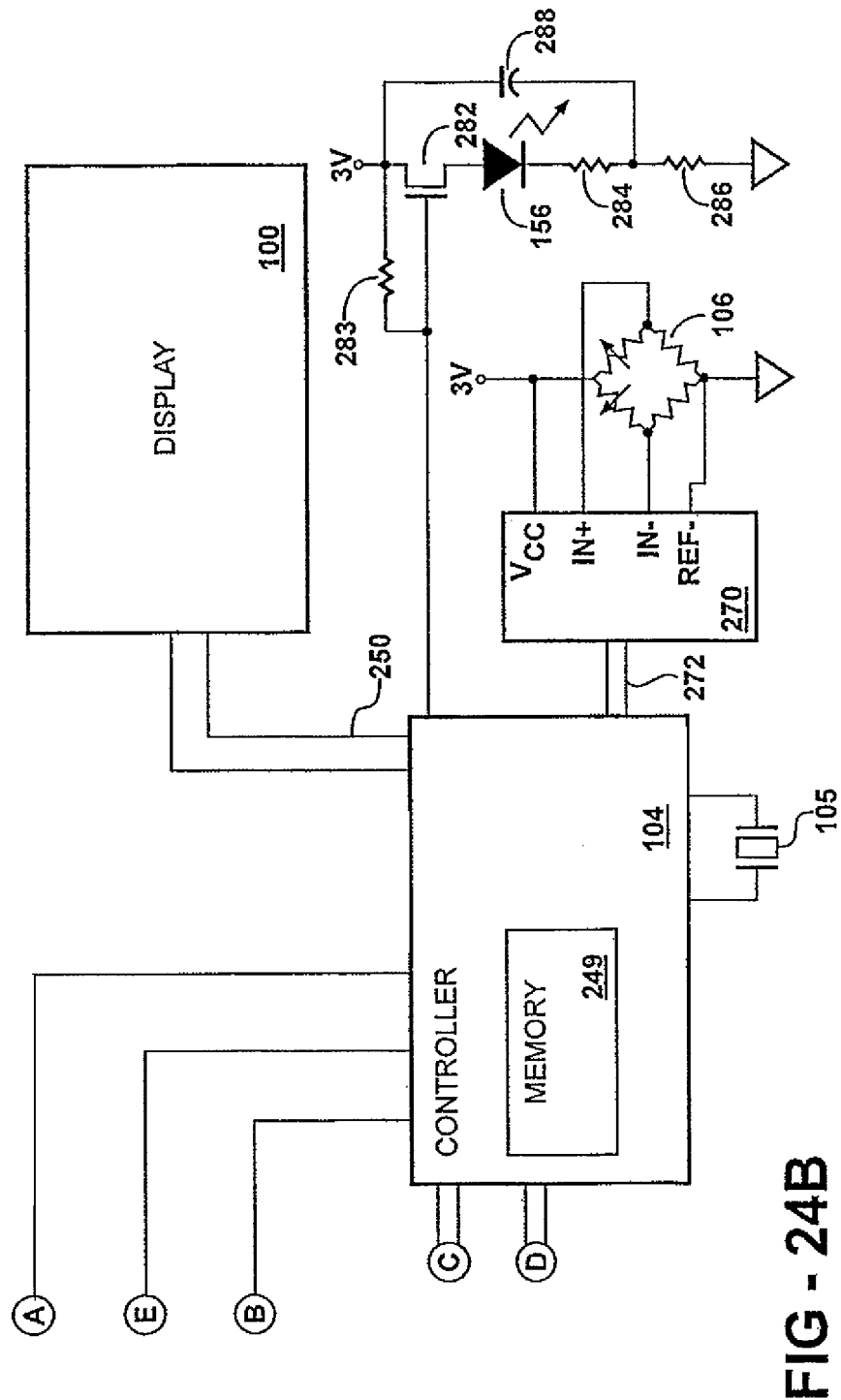

FIGS. 24A and 24B, when assembled together, form a block and partial schematic diagram of the electronics integral with the fluid delivery device 30. The controller 104, in one version of the invention is an Atmel ATmega3290/V 8-bit Microcontroller with in system programmable memory available from the Atmel Corporation of San Jose, Calif. This particular controller 104, in addition to a CPU, has a 32 k byte flash memory, a 1 k byte EEPROM and 2 k bytes of RAM. Collectively, these memories as depicted as a single memory block 249 in FIG. 24B. A crystal 105 provides a clock signal to the controller 104. In one version of this invention, this signal is at a frequency of 3.6864 Hz. This controller 104 is also capable of driving a set of 4×40 LCD segments. In FIG. 24B, a bus 250 is shown connecting the controller 104 to the display 100. The display 100 preferably has a screen refresh rate of 350 mS or less.

Power to actuate the display 100, the controller 104, the pressure sensor 106, the volume sensor 108, and an LED 156 for transmitting data wirelessly to external devices (described further below), comes from two series connected batteries 124, called out with a single identification number. In one version of the invention the CR2016 lithium button cell battery available from Renata SA, Itingen/Switzerland are employed as the batteries 124. These batteries have an output potential (each cell) of 3 volts. The output potential across the batteries 124 is applied to a voltage regulator 254 to produce a constant DC voltage. In one version of the invention the FAN2500 100 mA CMOS LDO Regulator available from Fairchild Semiconductor of South Portland, Me., is employed as the voltage regulator 254.

The positive terminal of the series connected batteries 124 is applied to the VIN and Enable pins of the voltage regulator 254 through a FET 252. As long as the device remains off, there is no path to ground from the positive terminal of batteries 124. Consequently, there is no voltage drop across resistor 256. Since the voltages across the source and gate of FET 252 are equal, the FET is normally in the off state. This construction thus means that, as long as the fluid delivery device 30 is not actuated, there is only a nominal parasitic current flow out of the batteries 124. This current is in typically 100 nanoAmps or less. Consequently, over an extended period of time, the charge stored in the batteries does not deplete to the level below which the batteries are no longer able to actuate the power consuming components internal to the fluid delivery device 30. Thus, this power conserving circuitry allows the fluid delivery device 30 of this invention to remain stored and ready for use with the original batteries 124 for a period of time of often more than 6 months and, in some instances, 12 months or more.

The 3 VDC output signal produced by the voltage regulator 254 is output through the output pin. A capacitor 258, tied between the output and ground, filters the AC component from the output signal. Also in FIG. 24A is shown a capacitor 260 tied between the bypass pin of the voltage regulator 254 and ground. The capacitor 260 is provided to minimize the noise of the 3 VDC signal output by the voltage regulator 254. The actual adjustment of the output voltage of the voltage regulator 254 may be fixed at manufacture. Thus the need to provide voltage adjustment resistors is eliminated. FIG. 24A does illustrate the connection between the ground pin of the voltage regulator 254 and ground.

In FIGS. 24A and 24B, the application of the 3 VDC as the VCC signal to the controller 104 is shown as the A-A connection. To reduce drawing complexity, the rail along which the 3 VDC signal is available to other components is not shown.

Also seen in FIG. 24A are two series connected resistors 261 and 262 connected between the input pin of the voltage regulator 254 and ground. The voltage present at the junction of the resistors 261 and 262 is proportional to the potential across the batteries 124. The voltage at this junction is applied to the controller 104. As part of the control sequence, the controller 104 periodically compares this voltage to a reference voltage level. If the comparison indicates that the battery potential is below the reference level, the controller 104 asserts a low battery warning that is integral with display 100.

As discussed above, normally FET 252 is turned off so as to prevent current flow to the voltage regulator 254. Consequently, normally the controller 104 and the other components internal to the fluid delivery device 30 are in the off mode in which they do not draw charge from the batteries 124. The fluid delivery device 30 is turned on for use by depressing the on/recall switch 120. The on/recall switch 120 is a normally open push button switch tied between the gate of FET 252 and ground. In FIG. 24A, a diode 264 is located between the gate of FET 252 and the on/recall switch 120 wherein the cathode of the diode is directed towards the on/recall switch. The closing of the on/recall switch 120 ties the gate of FET 252 to ground. This zeroing out of the gate voltage turns FET 252 on so as to allow current flow to the VIN and Enable pins of the voltage regulator 254. The voltage regulator 254, in turn, outputs the 3 VDC signal. The application of the 3 VDC signal to the controller 104 as the VCC causes the actuation of the initialization module internal to the controller 104 so that the controller 104 turns itself on.

Shown connected across the diode 264 and the on/recall switch 120 is a normally off FET 266. The controller 104 applies a control signal to the gate of FET 266. This control signal is asserted as part of the initialization of the controller 104. This turning on of FET 266 thus ties the gate of FET 262 to ground once the fluid delivery device 30 is first turned on. Also seen in the Figures is a resistor 268 tied between the gate of FET 266 and ground.

While not illustrated, it should be understood that a software module running on the controller 104 is a time out monitor. If the controller 104 does not detect a change in the signals from one of the other devices connected thereto such as the pressure sensor 106, the volume sensor 108 or another one of 112, 114, 115, 116, 118 and 168 input devices (switches), the time out monitor initiates an internal program to save the recorded data and power down the fluid delivery device 30. In some versions of the invention, this power down process is initiated if the device has been inactive for a time period that may be set to be anywhere from 2 to 5 minutes; 3 minutes being common. The last part of this process is the negation of the control signal to FET 266. The negation of this control signal causes FET 252 to return to its normally off state so as to prevent further draining of the charge stored in the batteries 124.

Collectively, because there is only parasitic depletion of the charge stored in the batteries 124 when the device is in deactivated storage, and the time out monitor deactivates the fluid delivery device 30 after a period on non use only the relatively small sized batteries are required. The small size and weight of the batteries contributes to the minimization of the overall size and weight of the fluid delivery device 30.

Input devices 112, 114, 115, 116, 118 and 168 are depicted in FIG. 24A as a set of normally open switches. Each switch (device) has one end tied to ground. The opposed ends of the switches are tied to separate pins of the controller 104. In the Figures this connection is established over a bus 269. A voltage source internal to the controller 104 (source not illustrated) applies a logical HIGH signal to each device (switch) internal to the controller 104. When any particular device (switch) is momentarily depressed, (switch closed) the signal present at the associated controller pin is pulled to ground. Thus a logical LOW signal is sensed at the pin when the associated switch is closed.

Also shown as a switch tied between a pin of controller 104 and ground is engagement detector 152. When the engagement mechanism 56 is in the engaged state, the switch of engagement detector 152 is closed. This pulls the signal present at the associated pin of controller 104 LOW. Based on the assertion of this LOW signal, a processing module internal to the controller allows the processing module that generates volume data to execute and output volume measurement data.

The pressure sensor 106 is schematically depicted in FIG. 24A. As described above, the 26PCFFS2G±100 psi Gage/Vacuum Gage Sensor from Honeywell Sensing and Control, Freeport, Ill., functions as the pressure sensor 106. This particular pressure sensor 106 includes a piezo-resistive sensing element. The pressure sensor 106 itself is constructed as a Wheatstone bridge. The 3 VDC signal is applied to the pressure sensor 106. The opposed end of the pressure sensor 106 is tied to ground. The potentials across the resistive elements of the pressure sensor 106 are applied to the opposed IN+ and IN− input pins of a differential input $\Delta\Sigma$ analog to digital converter (ADC) 270. One such ADC 270 is the LTC2433-1 ADC available from Linear Technologies of Milpitas, Calif. As also seen in the Figures, the ground point of the pressure sensor 106 is tied to the REF input pin of the ADC 270.

This particular ADC 270, outputs a digitized representation in the difference between the voltages across the opposed ends of sensor 106 as a serial bit stream. This data stream is output with a clock signal. In FIG. 31B these signals are shown as being applied to the controller 104 over a multi-wire bus 272.

The volume sensor 108 is also schematically illustrated in FIG. 24A. The four sensing members 150 are depicted as contacts 150a, 150b, 150c and 150d. The contact member 146 is shown as a wiper that rotates and that can electrically connect any two of the adjacent contacts. Contact 150a is tied to ground. The 3 VDC signal is applied to contact 150b through a resistor 274. The signal present at the junction of contact 150b and resistor 274 is applied to an input pin of the controller 104. In the Figures, this signal is shown as being applied to controller 104 through a conductive path that is part of bus 276. The 3 VDC is also applied to contact 150c through a resistor 278. The signal present at the junction of contact 150c and resistor 278 is applied back to an input pin of controller 104 through a second conductor integral with bus 278. Contact 150d is also tied to a pin of controller 104.

Figure 25:
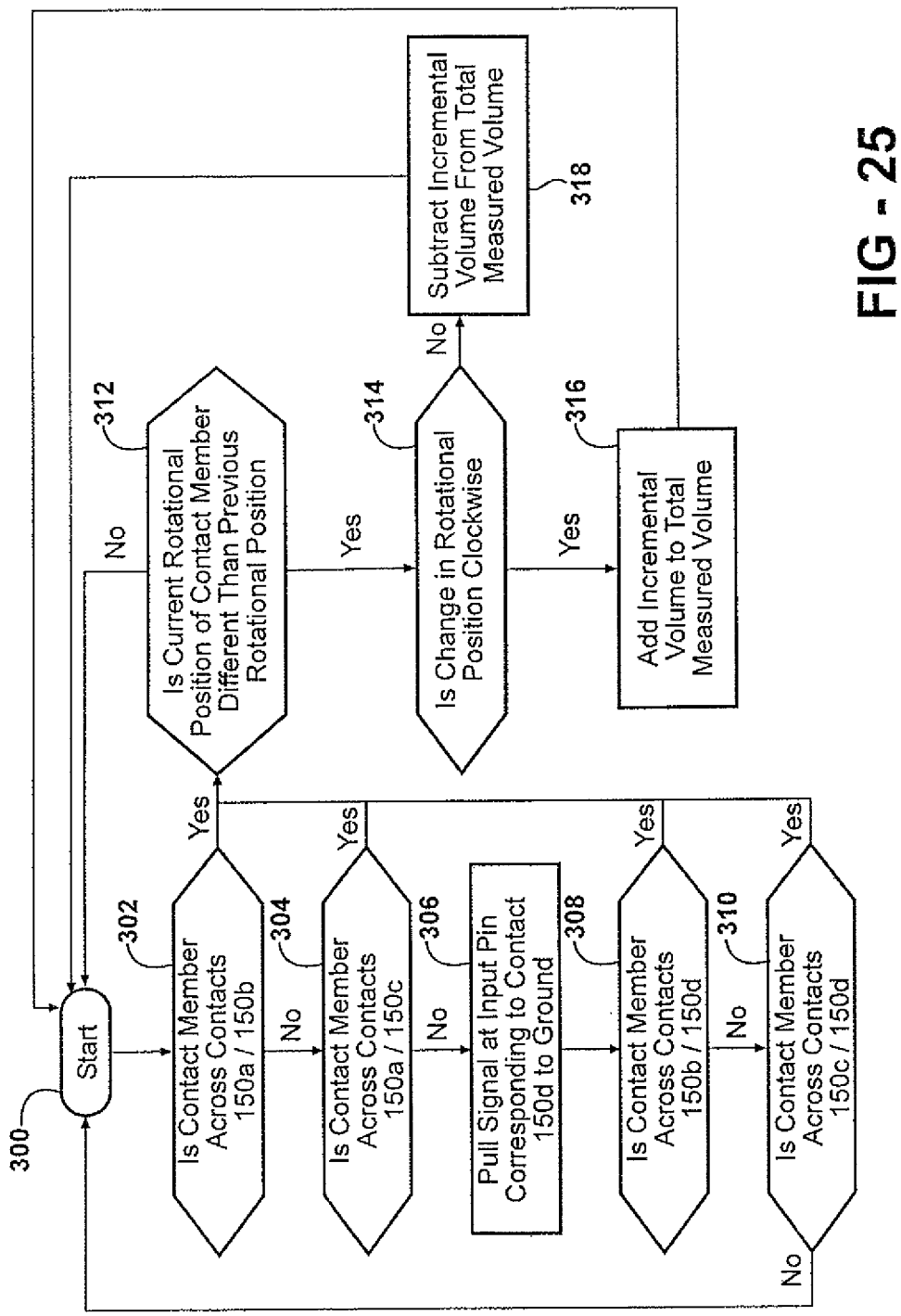
FIG. 25 is an flow chart illustrating steps carried out by a controller of the fluid delivery device to measure volume.

Referring to FIGS. 24A and 25, the controller 104 is configured to periodically perform illustrated steps 302-318 to carry out volume measurement. In essence, the volume measurement sequence is carried out by the controller 104 by sequentially checking signals at the controller 104. In a first step 302, the controller 104 determines whether the contact member 146 is at a first rotational position that electrically connects contact 150a and contact 150b by detecting the signal at the input pin of the controller 104 corresponding to contact 150b. If the contact member 146 is in this first rotational position, across contacts 150a and 150b, then the signal present at the input pin will be drawn to ground by contact 150a. The controller 104 will recognize this as indicating that the contact member 146 is across contacts 150a and 150b.

From here, the controller 104 will proceed to determine whether the total volume should be increased or decreased in steps 312-318 (described below).

If the contact member 146 is not at this first rotational position, then the signal at the input pin corresponding to contact 150b will remain HIGH and the controller 104 will move to the second step 304. In the second step 304, the controller 104 next determines whether the contact member 146 is at a second rotational position that electrically connects contact 150a and contact 150c by detecting the signal at the input pin corresponding to contact 150c. This second step 304 is carried out in precisely the same manner as the first step 302.

If the contact member 146 is not at this second rotational position, across contact 150a and contact 150c, then the controller 104 internally pulls contact 150d to ground in a third step 306. Then, in a fourth step 308, the controller 104 again checks the signal at the input pin corresponding to contact 150b to look for the same type of effect looked for in the first step 302, i.e., the signal present at the input pin is pulled to ground. If so, then the contact member 146 is at a third rotational position, across contact 150b and contact 150d. If not, then the controller 104 moves to a fifth step 310 to check the signal at the input pin corresponding to contact 150c to look for the same type of effect looked for in the second step 304, i.e., the signal present at the input pin is pulled to ground. If so, then the contact member 146 is at a fourth rotational position, across contact 150c and contact 150d.

If the controller 104 does not detect that that the contact member 146 is at any of the four rotational positions, then the contact member 146 is determined to be at a neutral position (between rotational positions, not in contact with any two of the contacts 150a, 150b, 150c, 150d) and the volume measurement sequence is restarted at start 300. If the contact member 146 is detected at any one of the rotational positions across two adjacent contacts 150a, 150b, 150c, 150d, and a current rotational position of the contact member 146 has changed from a previously detected rotational position (see step 312), then the controller 104 either adds (contact member 146 has shifted one rotational position clockwise) or subtracts (contact member 146 has shifted one rotational position counterclockwise) an incremental volume value (here 0.125 mL) to a total measured value displayed on the display 100. This is shown in steps 314-318. The controller 104 is configured to carry out the volume sensing sequence once every 555 μs. In other words, volume measurement is preferably not carried out continuously.

IR transmitting LED 156 is actuated by the controller 104. As seen in FIG. 24B, the LED 156 is connected to the source of FET 282. The drain of FET 282 is connected to the 3 VDC rail. The 3VDC signal is also applied to the gate of FET 282 through a resistor 283. The gate of FET 282 is also tied to a pin of the controller 104. The cathode of the LED 156 is tied to ground through two series connected resistors 284 and 286. A capacitor 288 is tied between the 3 VDC rail and the junction of resistors 284 and 286.

Normally, the current present at the gate of FET 282 holds FET in the non-conducting state. The controller 104 actuates the LED 156 by tying the gate of FET 282 to ground, connection not shown. This results in the turning on of FET 282 so there is current flow there through. When FET 282 is turned on, the charge stored across capacitor 288 flows through the FET 282 so as to increase the current flow through the LED 156. This reduces the power the batteries 124 need to provide in order to energize the LED 156.

Referring back to FIG. 4, an engagement detector 152 is in communication with the controller 104 and responsive to the engagement mechanism 56 to detect when the engagement mechanism 56 is in the engaged position E, i.e., the plunger 52 can only be advanced via rotation. The controller 104 is configured to measure the volume of the fluid delivered from the fluid chamber 46 only when the engagement mechanism 56 is in the engaged position E. When the engagement detector 152 indicates that the engagement mechanism 56 is in the engaged position E, volume measurement is carried out and the volume delivered is displayed on the display 100. When the engagement detector 152 indicates that the engagement mechanism 56 is in the disengaged position D, volume measurement discontinues and the volume delivered is not shown on the display 100.

In other embodiments, the engagement detector 152 is a reed switch (not shown) that senses a magnet (not shown) in the slide member 58 when the threads 54 are disengaged. In some embodiments, the controller 104 resets the volume each time the slide member 58 moves from the engaged position back to the disengaged position.

Data Transfer

Figures 26, 27:
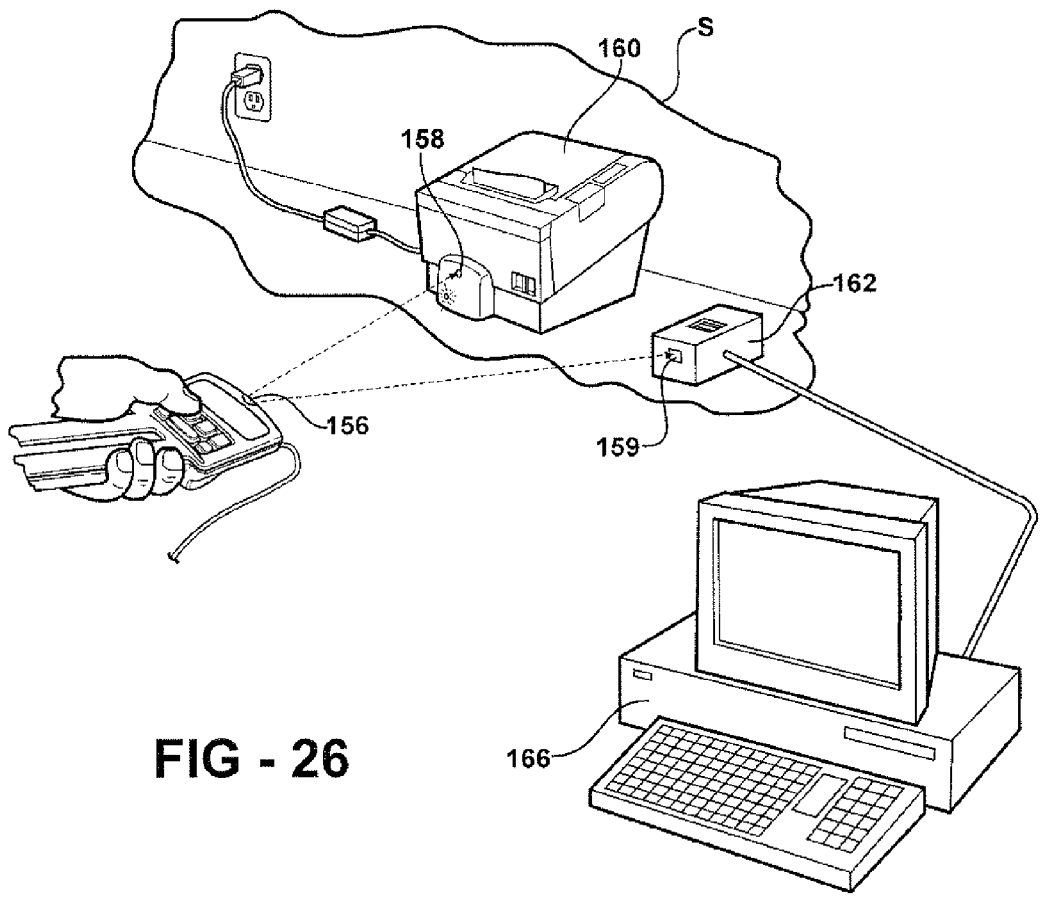
FIG. 26 is a perspective view illustrating a printer and an external module for use with the fluid delivery device of the present invention to transfer data from the fluid delivery device to the printer or a remote processing station through the external module.
FIGS. 27-29 are illustrations of sample data output from the printer.

In some embodiments, the fluid delivery device 30 includes a communication module 154 (see FIG. 23) supported on the main PCB 122. The communication module 154 is in communication with the controller 104 to communicate the stored data from the controller 104 to an external device such as a printer 160 or external module 162, as shown in FIG. 26. The communication module 154 preferably includes a wireless transmitter 156 (see FIG. 26) for wirelessly transmitting the data from the controller 104. In the embodiment shown, the wireless transmitter 156 is the IR-transmitting LED 156 operating under principles of infrared communication. Of course, communication with the printer 160 or external module 162 can take many known variations. Communication can be wireless using standard methods such as IR or RF.

When communicating with the printer 160 or the external module 162, data is compressed or encrypted prior to being sent to the printer 160 or the external module 162. The printer 160 or external module 162 then expands the data and puts it into the desired format for printing or for further data transfer. This method serves to minimize the transmission between the fluid delivery device 30 and the printer 160 or the external module 162. It also saves memory space on the controller 104. Both the printer 160 and external module 162 include a wireless receiver 158, 159 (IR sensor in one embodiment) for receiving the data from the wireless transmitter 156. The external module 162 may include a microprocessor with memory for receiving, processing, and temporarily storing the data received from the fluid delivery device 30. More preferably, the external module 162 is configured to process the data from the communication module 154 into a form usable by a remote processing station 166, such as a computer electronically connected to the external module 162 using a USB cable or other electronic coupling methods. Software is loaded on the remote processing station 166 to view, monitor, or manipulate the data received from the fluid delivery device 30 via the external module 162.

In use, the fluid delivery device 30 (preferably a sterilized, single use item) is placed in a sterile field. The external module 162 (and printer 160) is placed outside of the sterile field (shown by the boundary S). The external module 162 then receives the data from the fluid delivery device 30 when the user presses a data transfer switch 168 on the keypad 110. This method of use is particularly advantageous during medical procedures to keep the external module 162 outside of the sterile field and eliminate the need to sterilize such devices. It should be appreciated that the data could be directly transferred to the remote processing station 166 from the fluid delivery device 30 in the event the remote processing station 166 is internally equipped with a device similar to the external module 162.

The fluid delivery device 30 could also be configured for communicating with a docking station (not shown) to download data to the printer 160, or to a jump drive through a USB port, etc. Communication with the docking station can be through electrical contacts or near field communication such as RF, IR, or inductive coupling.

Figure 28:
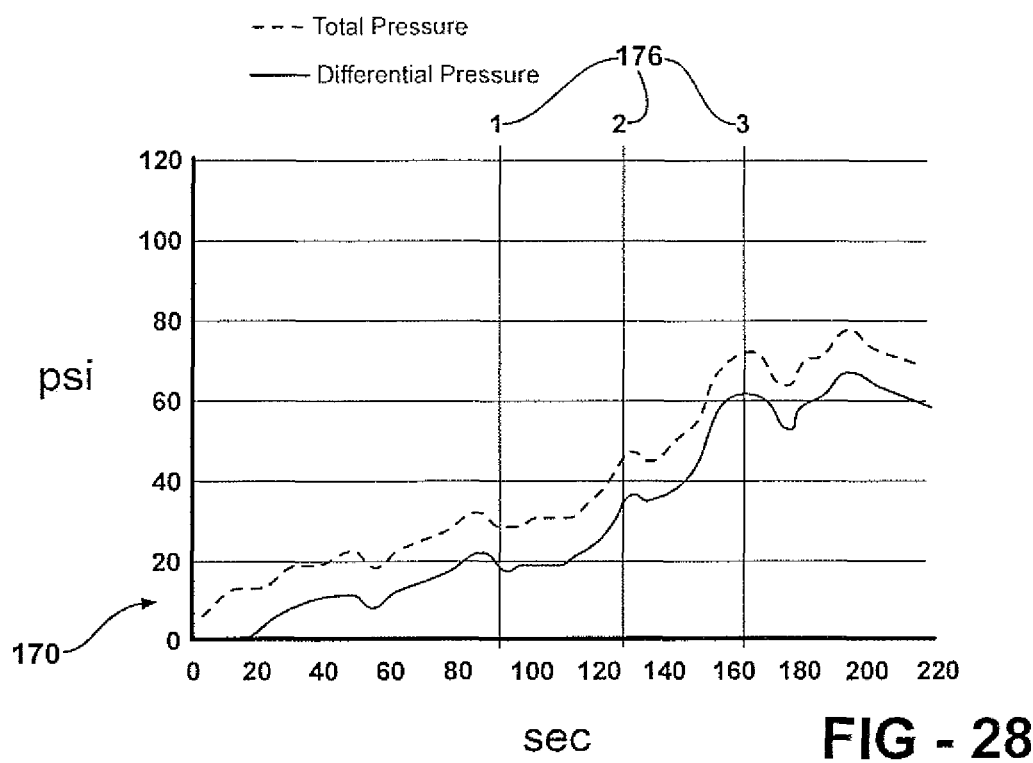
Figure 29:
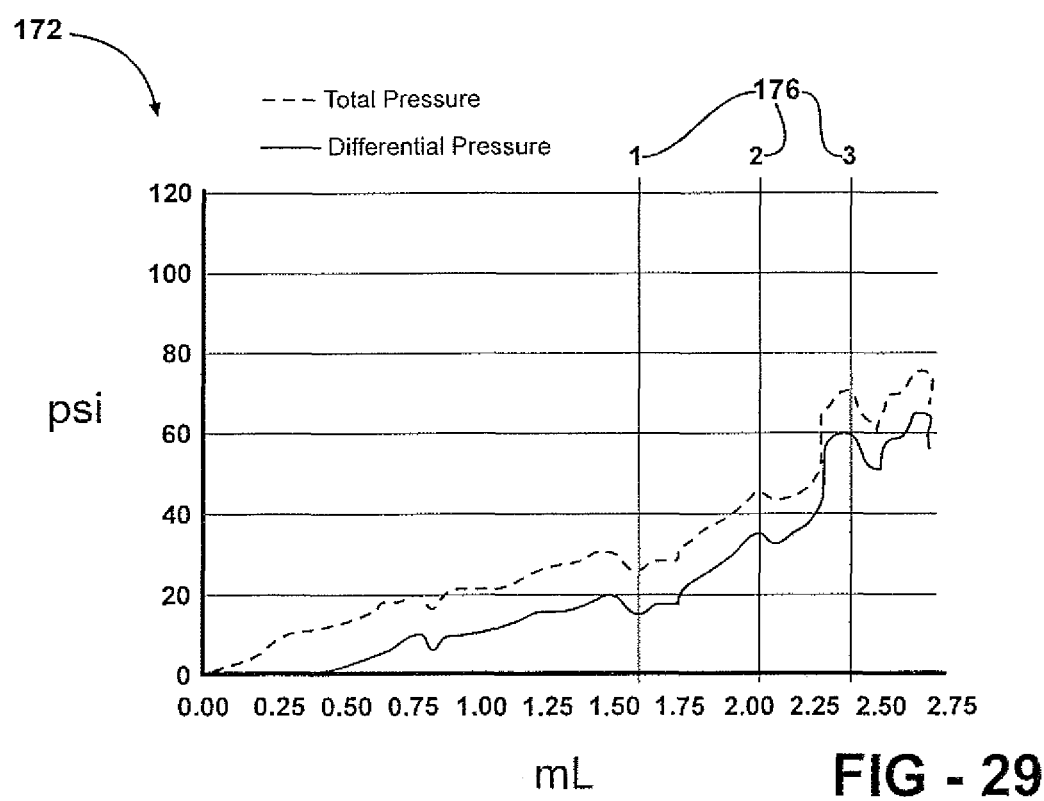

When the data is transferred to the printer 160 (by also selecting the data transfer switch 168 or another switch on the keypad 110), the data can be represented in a table 174 or graphical format 170, 172. Samples of the various tables 174 and graphs 170, 172 that can be used are shown in FIGS. 27-29. The data that is represented on the printouts can include manually and automatically saved data, e.g., data from key data points for each event, and/or automatically saved data such as maximum pressure, maximum volume, maximum time, zeroed pressure, and zeroed volume.

Print results can include, for example, a pressure vs. time graph 170, a volume vs. time graph (not shown); a pressure vs. volume graph 172; a table 174 of manually and automatically saved data; marked locations 176 of saved key data points on the graph (see points 1, 2, and 3), and a separate printout specific to an event or disc number so that separate tables and graphs can be obtained for each event or disc evaluated. In the disclosed embodiment, each graph has the same scale on separate axes so the results can be easily compared.

In one embodiment, the pressure, volume, and/or time can be correlated to one metric, such as a slope, for quicker and easier reading and evaluation by a physician. The controller 104 is configured to determine this composite metric based on the pressure, volume, and time, or any combination of at least two of these parameters. The controller 104 could also display the composite metric on the display 100 such as by status bars 178 that gradually fill to indicate a rise in value of the composite metric (see FIG. 19). In one embodiment, the composite metric is the value of the pressure divided by the value of the volume. In another embodiment, the composite metric is the value of the volume divided by the value of the time. In other embodiments, the composite metric is the change is pressure divided by the change in volume or the change in volume divided by the change in pressure. It should be appreciated that other variations for the composite metric could also be contemplated.

Discography and Pain Detection

Figures 30C, 30D:
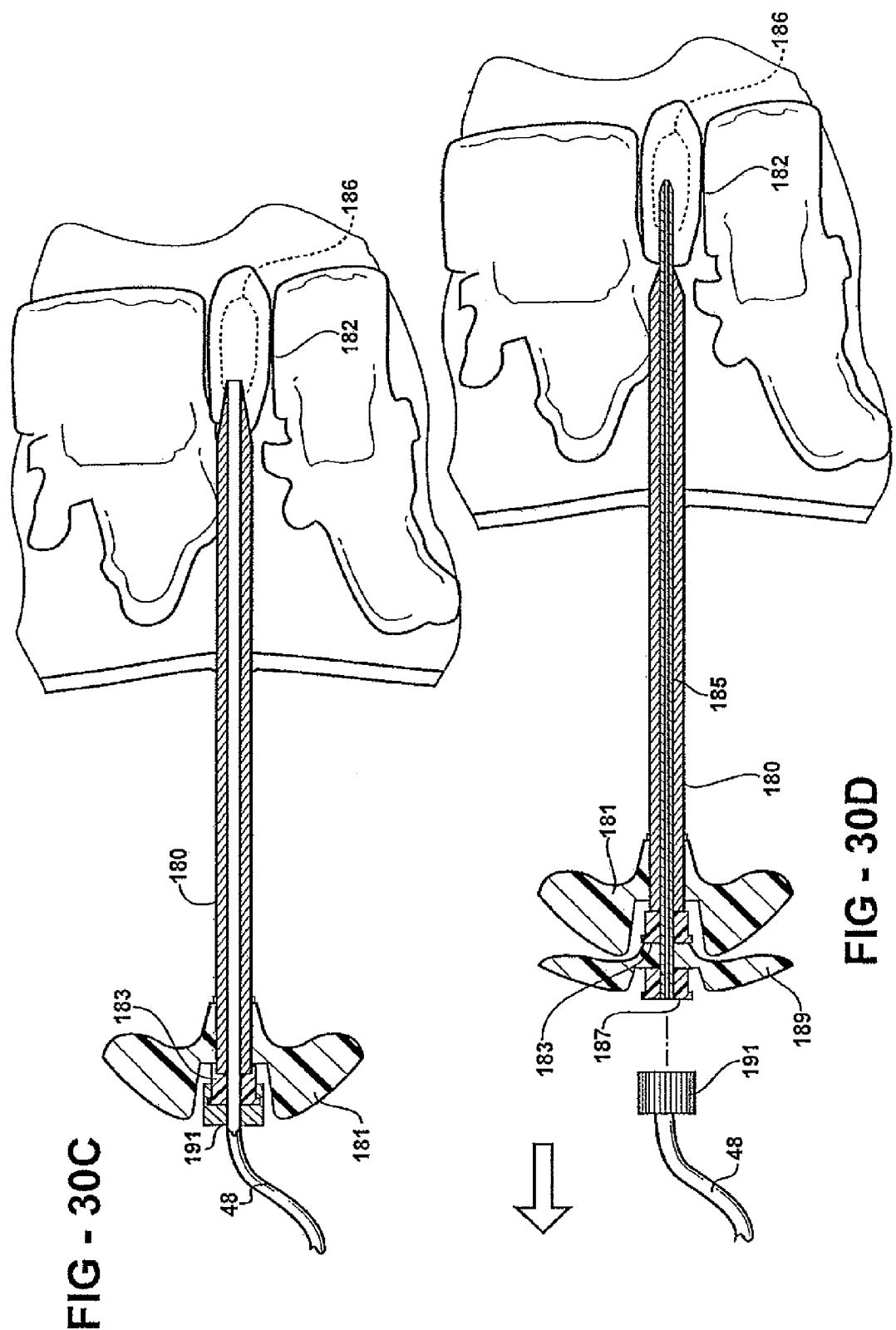

Referring to FIGS. 30A-30C, the fluid delivery device 30 is shown for use in discography. In discography, an introducer needle 180 is first placed percutaneously in the intervertebral disc 182 to be evaluated. A handle 181 is fixed to a proximal end of the introducer needle 180 to assist the user in placing the introducer needle 180 in the disc 182. FIG. 30A illustrates inserting the introducer needle 180 in the disc 182. In the embodiment shown, a stylet 184 is used to insert the introducer needle 180 into the disc 182 and place a distal end of the introducer needle 180 at a nucleus 186 of the disc 182. A cap 190 is fixed to a proximal end of the stylet 184. The cap 190 may be configured to lock to the handle 181 of the introducer needle 180 to facilitate insertion of the introducer needle 180 in the disc 182. The cap 190 may lock to a luer connector 183 and the handle 181 in the manner shown in U.S. Patent Application Publication No. 2004/0127814 to Negroni, which is hereby incorporated by reference. FIG. 30B illustrates the introducer needle 180 placed in the disc 182 with the stylet 184 being removed and FIG. 30C illustrates the connection of a threaded luer-lock connector 191 of the tube set 48 to the luer-lock connector 183 to allow the fluid to be delivered from the fluid delivery device 30 to the introducer needle 180.

Referring to FIG. 30D, in an alternative method, the introducer needle 180 is first percutaneously placed adjacent to the disc 182 without penetrating the disc 182. A separate delivery needle 185 is then inserted (with a separate delivery needle stylet, not shown) in the introducer needle 180 to penetrate the disc 182. FIG. 30D illustrates the delivery needle 185 in place after the delivery needle stylet (not shown) has been removed from the delivery needle 185. Once a distal end of the delivery needle 185 is properly positioned in the disc 182, as shown in FIG. 30D, the threaded luer-lock connector 191 of the tube set 48 is connected to a luer-lock connector 187 on a handle 189 fixed to the delivery needle 185. The handles 181, 189 could be locked together in the manner shown in U.S. Patent Application Publication No. 2004/0127814 to Negroni, which is hereby incorporated by reference. In some embodiments, a 3-way valve is used with the tube set 48 to control filling of the fluid chamber 46 and delivery of the fluid from the fluid chamber 46 to the delivery needle 185. Regardless of the method utilized, the introducer needle 180, when used alone (FIGS. 30A-30C), or with the delivery needle 185, referred to collectively as discography needles, preferably have an outside diameter of 16 gauge or smaller, e.g., 18 gauge or smaller, or even 20 gauge or smaller, etc., and a length of 5 cm or longer. Some discography needles 180, 185 have an outside diameter of 18 gauge or smaller and/or a length of 12 cm or longer. Alternative introducer needles that do not include handles may alternatively be employed.

During use in discography, the plunger 52 forces the fluid from the fluid delivery device 30 into and though the discography needle 180, 185 to the disc 182. The fluid chamber 46 of the fluid delivery device 30 preferably contains a contrast media. The contrast media is a fluid that is opaque to x-rays and thus provides an image of the interior structure of the patient's disc 182 in x-ray photographs or under fluoroscopy. The contrast media is pressurized by turning the handle 57 of the plunger 52 to rotate the plunger 52. The plunger 52 then moves in the fluid chamber 46 of the syringe barrel 44. When the plunger 52 moves in the fluid chamber 46, the fluid is pressurized and forced from the discography needle 180, 185 into the disc 182. The pressure within the syringe barrel 44 increases as the fluid fills the disc space. If there is a problem with the disc 182, the patient will experience pain. Or, in the event that there is a rupture in the disc 182, the patient may not experience pain, but the amount of fluid injected without a resultant increase in pressure will indicate a rupture. In discography, the fluid delivery device 30, its plunger, is preferably configured to deliver the fluid at a maximum pressure of up to 180 psi and in some versions up to 200 psi. The controller 104 may activate an alarm, either audible or visual, when the pressure exceeds a predetermined limit or limits. In one version of the invention, an alarm module executed by controller 104 continually monitors the total pressure of the fluid discharged by the device. When this pressure exceeds 100 psi, this module causes both the total and differential pressure presentations on the display to flash. When the total pressure exceeds 120 psi, the alarm module asserts output signals that causes both pressure presentations to display a HI message to the user.

During discography, the user may desire to accurately measure the amount of pain experienced by the patient. As discussed in the background, the patient typically calls out the amount of pain based upon a scale of 1 to 10. To better ensure diagnosis, more accurate methods of measuring pain are needed. Applicants have developed several methods that can be used in conjunction either directly, i.e. actually feeding directly into the fluid delivery device 30, or indirectly, i.e., physician input based upon the information generated from the patient.

One method would be to allow the patient to enter a pain magnitude response by, for example, squeezing a bulb (not shown). This would be considered a voluntary pain response, or a response that that patient is, to some extent, capable of controlling. The amount of pressure applied by the patient to the bulb would be registered and recorded in the fluid delivery device 30 as well as being displayed on the fluid delivery device 30. For example, the readout may be in the form of a moving graph that shows the level of pain, i.e., the amount of pressure applied to the bulb by the patient, as a spike on the graph or a light indicator with varying colors, change of the backlight color, or a status bar of pain indication, etc.

Another method would be the collection of unsolicited pain responses from a patient based on changes in physiological parameters such as body temperature, blood pressure, muscle flex, heart rate, respiration, oxygen saturation, integumentary system, muscle tone, intracranial pressure, pupil size, vagal nerve tone, hormonal release, metabolic changes, brain waves, and the like. These are involuntary pain responses that are largely uncontrollable by the patient thereby reducing false pain indications, as opposed to the squeeze bulb embodiment described above, which could result in false pain indications. This data would be either individually displayed, or displayed as a pain magnitude based upon a pre-determined pain magnitude scale corresponding to specific data. The display types would be similar to those discussed above with the physical action, i.e., bulb squeezing by the patient.

In this embodiment, a physiological sensor 192 is used to monitor the changes in the physiological parameters. The physiological sensor 192 is placed in communication with the controller 104 for sensing the physiological parameter of the patient, e.g., body temperature, blood pressure, muscle flex, etc. Thus, the physiological sensor 192 may be one or more of a blood pressure sensor, a body temperature sensor, a muscle displacement sensor, etc. A plurality of physiological parameters could be monitored at the same time with multiple physiological sensors 192 with pain indicated when a combination of changes is detected. The pain magnitude could also be correlated to a predetermined algorithm utilizing these parameters.

The controller 104 is configured to automatically mark key values of the pressure, volume, and time in response to the physiological parameter(s) exceeding a predetermined limit, i.e., without the need for the physician to press the save button. Values of the physiological parameter(s) or corresponding pain magnitude can be displayed, saved, and printed vs. pressure, volume, and/or time. In this embodiment, the controller 104 is configured to display the value of the physiological parameter on the display 100. These values can also be highlighted on the printouts for ease of reading.

Figure 31:
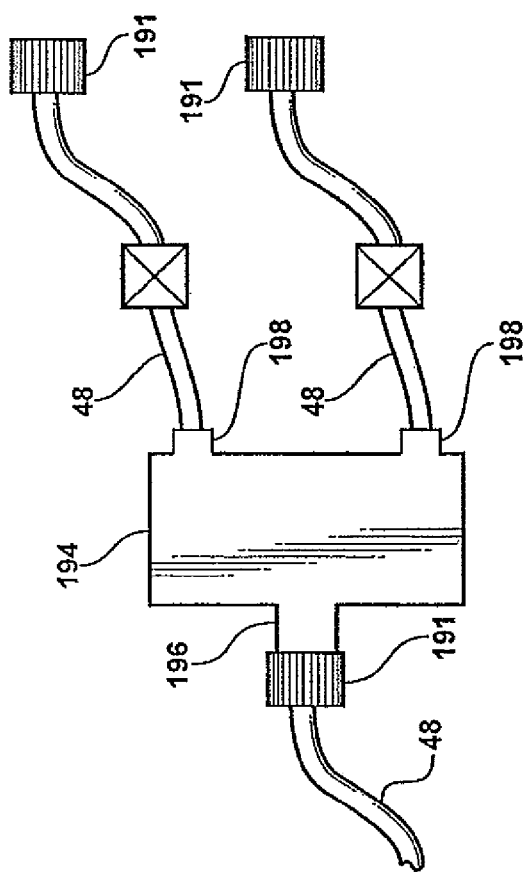
FIG. 31 is a side view of a manifold for use with the fluid delivery device.

In some embodiments, referring to FIG. 31, a manifold 194 can be used to split the fluid delivered from the fluid delivery device 30 into multiple tube sets 48. In this embodiment, the manifold 194 includes an inlet 196 in fluid communication with the fluid chamber 46 and a plurality of outlets 198 for directing the fluid to multiple discography needles 180, 185. By using a stopcock (shown as a valve in FIG. 31), any number of the discography needles 180, 185 can be shut-off from fluid delivery such that the fluid is delivered to only one discography needle 180, 185 at a time. The patient may also remain unaware of which disc 182 the fluid is being delivered to, thus better isolating the disc causing the patient's back pain and reducing false pain indications from the patient.

As discussed above, the fluid delivery device 30 is sized to allow a user to hold it in single hand. Given the relatively light weight of the device the user can hold it in his/her hand for an extended period of time without tremor-inducing fatigue developing in either the hand or supporting arm. Furthermore, since the pressure and volume information are presented on the device, the user does not have to divert his or her eyes to a remote display in order to view these parameters. Collectively, this means the user can focus his/her mental effort on the more important aspects of the procedure: manipulating the handle; monitoring the pressure and volume of fluid being delivered; and the response of the patient.

Other Uses

The fluid delivery device 30 of the present invention may also be utilized in other procedures in which the measurement of both pressure and volume in a lightweight, hand-held device may be useful. Examples of such procedures include vertebroplasty, kyphoplasty, and angioplasty. For illustration purposes, the use of the fluid delivery device 30 in vertebroplasty, kyphoplasty, and angioplasty is shown in FIGS. 32-34, respectively.

Figure 32:
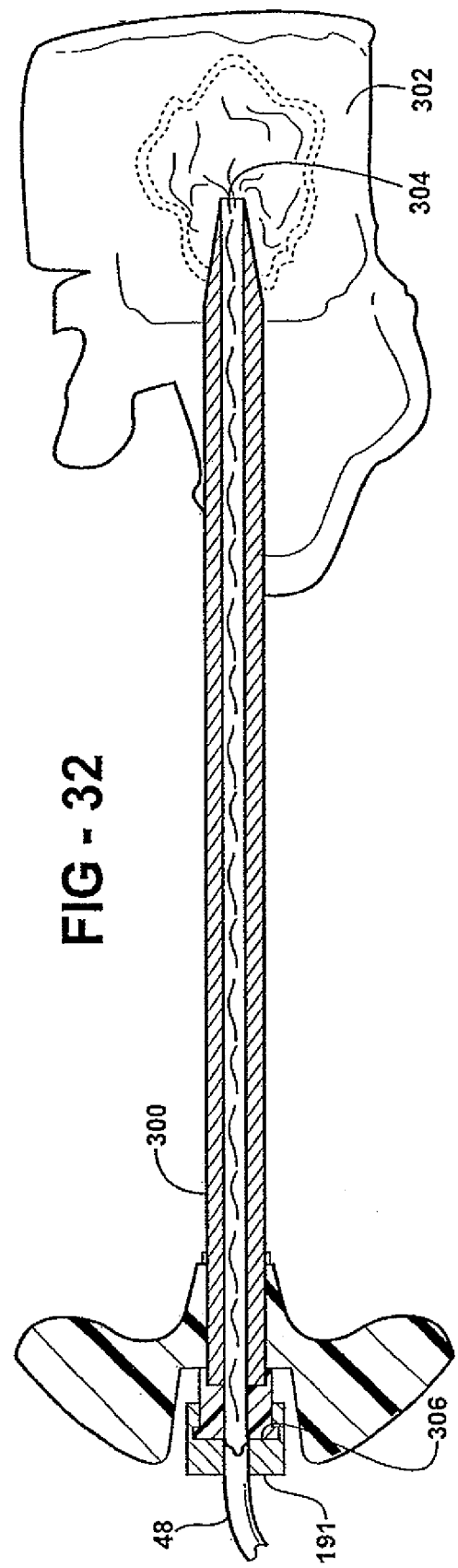

Referring to FIG. 32, in vertebroplasty, an introducer needle 300 is placed in a vertebral body 302 using the technique previously described with respect to discography. More specifically, a distal end 304 of the introducer needle 300 is placed inside the vertebral body 302 at a target site. The fluid delivery device 30 is then connected to a proximal end 306 of the introducer needle 300 via the threaded luer-lock connector 191. In this case, the fluid delivered may be a flowable material capable of setting to a hardened condition such as PMMA bone cement, hydrogel, or the like. The introducer needle 300 used for vertebroplasty preferably has an outer diameter of 13 gauge or larger.

Referring to FIG. 33, in kyphoplasty, an inflatable member 400 is positioned in the vertebral body 302 through an access cannula 402 using methods well known to those skilled in the art. The inflatable member 400 is connected to a distal end of an inflation catheter 404. The fluid delivery device 30 is connected to a proximal end of the inflation catheter 404 by the threaded luer-lock connector 191 to provide fluid communication between the fluid delivery device 30 and the inflatable member 400 to inject the fluid (such as contrast media) into the inflatable member 400. The inflatable member 400 may be a balloon that expands as fluid is delivered, under pressure, into the inflatable member 400. In this procedure, the fluid delivery device 30 is preferably configured to deliver the fluid into the inflatable member 400 at pressures of 300 psi or greater, more preferably at pressures of from 300 to 450 psi. The access cannula used to provide access to the vertebral body 302 for the inflatable member 400 preferably has an outer diameter of 13 gauge or larger.

Referring to FIG. 34, in angioplasty, an inflation catheter 500 with a balloon 502 at a distal end thereof is placed in a partially blocked blood vessel 504 at a lesion 506 to compress the lesion 506 and improve blood flow in the vicinity of the lesion 506. The fluid delivery device 30 of the present invention is connected to a proximal end of the inflation catheter 500 to provide fluid communication between the fluid delivery device 30 and the balloon 502 to inject the fluid into the balloon 500. In this procedure, the fluid delivery device 30 is preferably configured to deliver the fluid into the balloon 500 at pressures of 300 psi or less, more preferably at pressures of 200 psi or less, and most preferably at pressures of 175 psi or less.

The illustrated and disclosed handle 57 is understood to be illustrative and not limiting of the types of manual actuators that may be used to actuate the plunger 52. For example, a rotating knob that drives a geared shaft may perform this function. Also a lever assembly may be used in still other versions of this invention.

Similarly, the shape of the housing 32 is again understood to be exemplary, not exclusionary. In an alternative construction of the invention, the housing is generally pistol shaped. In this version of the invention, the fluid chamber and plunger are located in the barrel section. The manual actuator may take the form of a lever assembly wherein the lever arm extends forward from the handgrip portion of the housing in a manner similar to a trigger. In this version of the invention, the display may be a section of the housing that extends upwardly at an angle from the barrel section. Likewise, the position of the batteries within the housing may change from what has been described.

Likewise this invention is not limited to delivery devices wherein a plunger contained in the fluid chamber provides the motive force for pumping the fluid out of the chamber. In alternative versions of the invention, other pumping devices may be used to force the fluid through the introducer needle 180. Thus, in one potential alternative version of the invention, the pump may be a bellows pump. Either gravity or suction pressure causes the fluid in the fluid chamber (fluid reservoir) to flow into the pump. In a compression cycle, the fluid is forced through the introducer needle 180.

From the above description it should likewise be clear that alternative transducers may be used to monitor the pressure or volume of the fluid applied to the target site (disc 182, vertebral body 302, or catheter balloon 502). For example, in the above described version of the invention, capacitance sensing may be used to monitor plunger rotation. In this version of the invention, the capacitance between a fixed plate or plates and a plate or plates that rotate with the plunger may be monitored to provide an inferential indication of plunger extension and retraction. Alternatively, a Hall sensor that monitors a magnet attached to the moving head of the pump assembly may be used to monitor the extension and retraction of the pump head. Alternatively a transducer that varies capacitance as a consequence of plunger or pump head displacement may be used to provide a measure of fluid displacement. Again the monitoring of this movement would provide an inferential measure of the volume of fluid pumped to the target site. A volume sensor with a mechanical transducer such as a paddle wheel may even be employed. Likewise there is no requirement that, in all versions of the invention, the transducer employed to monitor fluid pressure be a piezo-resistive unit. This unit may be formed from piezoelectric material. In some versions of the invention a diaphragm type sensor may be employed as the pressure sensor.

Similarly, the disclosed circuit is understood to not be the sole possible circuit of this invention. Components different than the disclosed circuit may be employed. For example, in some versions of the invention there may be a processor and one or more separate memory chips.

Furthermore, in alternative versions of the invention, the wireless communications module may both transmit and receive signals. This may be useful so that the static device used to receive the data collected in the procedure returns an acknowledgement that the data are received. Also, during manufacturing, calibration information may be sent to the device for storage in the controller memory 249.

Obviously, other modifications and variations of the present invention are possible in light of the above teachings. The invention may be practiced otherwise than as specifically described within the scope of the appended claims.

What is claimed is:

1. A discography system for delivering fluid to an intervertebral disc through a fluid conduit during a discography procedure, monitoring selected parameters of the fluid delivered to the intervertebral disc, and transferring data related to the monitored parameters from inside the sterile field to outside the sterile field, said system comprising:
a fluid delivery device adapted for being placed within the sterile field to deliver fluid to the target site during the discography procedure, said device including:
a housing including a reservoir for storing the fluid, said housing having a hand-held portion;
a manually actuated pump disposed in said housing and configured to pump fluid from said reservoir, said pump including a manual actuator;
a discography needle connected to said housing for receiving the fluid discharged by said pump, said discography needle shaped for percutaneous insertion into the intervertebral disc to direct the fluid into the intervertebral disc and having a length of at least 5 cm and an outer diameter of 16 gauge or smaller diameter;
a pressure sensor disposed in said housing and positioned to sense a pressure of the fluid discharged by said pump, said pressure sensor producing a pressure signal representative of the sensed pressure;
a volume sensor disposed in said housing and positioned to sense a volume of the fluid discharged by said pump, said volume sensor producing a volume signal representative of the volume of the fluid discharged by said pump;
a controller disposed in said housing and connected to said pressure sensor for receiving the pressure signal and to said volume sensor for receiving the volume signal, said controller having memory for storing data related to said pressure signal and said volume signal and said controller configured to generate output signals associated with the stored data;
a display mounted to said housing and in communication with said controller for displaying values of pressure and volume;
a communication module in communication with said controller for receiving the output signals associated with the stored data, said communication module configured to generate transfer output signals associated with the stored data; and
a battery disposed in said housing for actuating said controller, said display, and said communication module;
in combination with:
a data transfer system adapted for being placed outside of the sterile field when said fluid delivery device is placed inside the sterile field, said data transfer system including an external device spaced from said fluid delivery device and configured for wirelessly receiving said transfer output signals from said communication module.

2. The system as set forth in claim 1, wherein said external device includes a printer.

3. The system as set forth in claim 1, wherein said external device includes a computer.

4. The system as set forth in claim 1, wherein said communication module includes an infrared LED capable of transmitting pulses of infrared light representative of the stored data.

5. The system as set forth in claim 1, including a data transfer switch in communication with said controller wherein said controller is configured to transfer the stored data to said external device in response to actuation of said data transfer switch.

6. The system as set forth in claim 1, wherein said housing, including said reservoir and said communication module, said manually actuated pump including said manual actuator, said pressure sensor, said volume sensor, said controller, said display, said communication module, and said battery cumulatively have a weight of 1.5 kilograms or less.

7. The system as set forth in claim 6, wherein said housing, including said reservoir and said communication module, said manually actuated pump including said manual actuator, said pressure sensor, said volume sensor, said controller, said display, said communication module, and said battery cumulatively have a weight of 0.5 kilograms or less.

8. The system as set forth in claim 1, wherein said pump is capable of discharging fluid into said discography needle at a maximum pressure of up to 200 psi.

9. The system as set forth in claim 1, wherein said discography needle has a length of at least 12 cm and an outer diameter of 18 gauge or smaller diameter.

\* \* \* \* \*